(12) United States Patent
Han et al.

(10) Patent No.: US 7,622,482 B2
(45) Date of Patent: Nov. 24, 2009

(54) CHEMICAL COMPOUNDS

(75) Inventors: Yongxin Han, Beijing (CN); Michelle Lamb, Waltham, MA (US); Peter Mohr, Boulder, CO (US); Bin Wang, Boulder, CO (US); Tao Wang, Waltham, MA (US); Dingwei Yu, Waltham, MA (US)

(73) Assignee: AstraZeneca, Sodertalje (SE)

( * ) Notice: Subject to any disclaimer, the term of this patent is extended or adjusted under 35 U.S.C. 154(b) by 86 days.

(21) Appl. No.: 11/816,376

(22) PCT Filed: Feb. 15, 2006

(86) PCT No.: PCT/GB2006/000522
§ 371 (c)(1),
(2), (4) Date: Oct. 19, 2007

(87) PCT Pub. No.: WO2006/087538
PCT Pub. Date: Aug. 24, 2006

(65) Prior Publication Data
US 2009/0137624 A1    May 28, 2009

Related U.S. Application Data

(60) Provisional application No. 60/732,965, filed on Nov. 3, 2005, provisional application No. 60/653,330, filed on Feb. 16, 2005.

(51) Int. Cl.
*A01N 43/42* (2006.01)
*A61K 31/44* (2006.01)
*C07D 471/00* (2006.01)
*C07D 487/00* (2006.01)
*C07D 471/02* (2006.01)
*C07D 491/02* (2006.01)
*C07D 498/02* (2006.01)

(52) U.S. Cl. .................. 514/300; 514/303; 514/393; 544/254; 544/255; 544/256; 546/113; 546/118

(58) Field of Classification Search ............... 544/254, 544/255, 256; 546/113, 118; 514/300, 303, 514/393
See application file for complete search history.

(56) References Cited

U.S. PATENT DOCUMENTS 6,699,994 B1 * 3/2004 Babu et al. ............... 546/306

* cited by examiner

*Primary Examiner*—D. Margaret Seaman
*Assistant Examiner*—Niloofar Rahmani

(57) ABSTRACT

This invention relates to novel compounds having the formula (I): and to their pharmaceutical compositions and to their methods of use. These novel compounds provide a treatment for cancer.

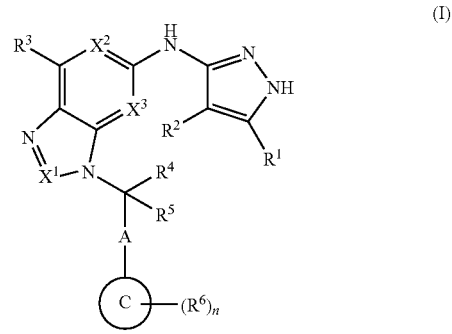

(I)

13 Claims, No Drawings

CHEMICAL COMPOUNDS

CROSS-REFERENCE TO RELATED APPLICATIONS

This application is a US National Stage under 35 U.S.C §371 of International Application No. PCT1 GB2006/000522 (filed Feb. 15, 2006) which claims priority under 35 U.S.C. §119 (e) to U.S. Provisional Application No. 60/653,330, filed on Feb. 16, 2005, and to U.S. Provisional Application No. 60/732,965, filed on Nov. 3, 2005.

FIELD OF THE INVENTION

The present invention relates to novel pyrazole derivatives, their pharmaceutical compositions and methods of use. In addition, the present invention relates to therapeutic methods for the treatment and prevention of cancers and to the use of these pyrazole derivatives in the manufacture of medicaments for use in the treatment and prevention of cancers.

BACKGROUND OF THE INVENTION

Receptor tyrosine kinases (RTK's) are a sub-family of protein kinases that play a critical role in cell signalling and are involved in a variety of cancer related processes including cell proliferation, survival, angiogenesis and metastasis. Currently up to 100 different RTK's including tropomyosin-related kinases (Trk's) have been identified.

Trk's are the high affinity receptors activated by a group of soluble growth factors called neurotrophins (NT). The Trk receptor family has three members—TrkA, TrkB and TrkC. Among the NTs there are (i) nerve growth factor (NGF) which activates TrkA, (ii) brain-derived growth factor (BDNF) and NT-4/5 which activate TrkB and (iii) NT3 which activates TrkC. Each Trk receptor contains an extra-cellular domain (ligand binding), a trans-membrane region and an intra-cellular domain (including kinase domain). Upon binding of the ligand, the kinase catalyzes auto-phosphorylation and triggers downstream signal transduction pathways.

Trk's are widely expressed in neuronal tissue during its development where Trk's are critical for the maintenance and survival of these cells. A post-embryonic role for the Trk/neurotrophin axis (or pathway), however, remains in question. There are reports showing that Trk's play important role in both development and function of the nervous system (Patapoutian, A. et al *Current Opinion in Neurobiology,* 2001, 11, 272-280).

In the past decade, a considerable number of literature documentations linking Trk signalling with cancer have published. For example, while Trk's are expressed at low levels outside the nervous system in the adult, Trk expression is increased in late stage prostate cancers. Both normal prostate tissue and androgen-dependent prostate tumours express low levels of Trk A and undetectable levels of Trk B and C. However, all isoforms of Trk receptors as well as their cognate ligands are up-regulated in late stage, androgen-independent prostate cancer. There is additional evidence that these late stage prostate cancer cells become dependent on the Trk/neurotrophin axis for their survival. Therefore, Trk inhibitors may yield a class of apoptosis-inducing agents specific for androgen-independent prostate cancer (Weeratna, A. T. et al *The Prostate,* 2000, 45, 140-148).

Furthermore, very recent literature also shows that over-expression, activation, amplification and/or mutation of Trk's are associated with secretory breast carcinoma (*Cancer Cell,* 2002, 2, 367-376), colorectal cancer (Bardelli et al *Science,* 2003, 300, 949-949) and ovarian cancer (Davidson, B. et al *Clinical Cancer Research,* 2003, 9, 2248-2259).

There are a few reports of selective Trk tyrosine kinase inhibitors. Cephalon described CEP-751, CEP-701 (George, D. et al *Cancer Research,* 1999, 59, 2395-2341) and other indolocarbazole analogues (WO0114380) as Trk inhibitors. It was shown that CEP-701 and/or CEP751, when combined with surgically or chemically induced androgen ablation, offered better efficacy compared with mono-therapy alone. GlaxoSmithKline disclosed certain oxindole compounds as Trk A inhibitors in WO0220479 and WO0220513. Recently, Japan Tobacco reported pyrazolyl condensed cyclic compounds as Trk inhibitors (JP2003231687A).

In addition to the above, Vertex Pharmaceuticals have described pyrazole compounds as inhibitors of GSK3, Aurora, etc. in WO0250065, WO0262789, WO03027111 and WO200437814; and AstraZeneca have reported pyrazole compounds as inhibitors against IGF-1 receptor kinase (WO0348133).

SUMMARY OF THE INVENTION

In accordance with the present invention, the applicants have hereby discovered novel pyrazole compounds, or pharmaceutically acceptable salts thereof, which possess Trk kinase inhibitory activity and are accordingly useful for their anti-proliferation and/or proapoptotic (such as anti-cancer) activity and in methods of treatment of the human or animal body. The invention also relates to processes for the manufacture of said pyrazole compounds, or pharmaceutically acceptable salts thereof, to pharmaceutical compositions containing them and to their use in the manufacture of medicaments for use in the production of an anti-proliferation and/or proapoptotic effect in warm-blooded animals such as man.

Also in accordance with the present invention the applicants provide methods of using such pyrazole compounds, or pharmaceutically acceptable salts thereof, in the treatment of cancer.

The properties of the compounds claimed in this invention are expected to be of value in the treatment of disease states associated with cell proliferation such as cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Furthermore, the compounds, or pharmaceutically acceptable salts thereof, of the invention are expected to be of value in the treatment or prophylaxis of cancers selected from congenital fibrosarcoma, mesoblastic nephroma, mesothelioma, acute myeloblastic leukemia, acute lymphocytic leukemia, multiple myeloma, melanoma, oesophageal cancer, myeloma, hepatocellular, pancreatic, cervical cancer, Ewings sarcoma, neuroblastoma, Kaposis sarcoma, ovarian cancer, breast cancer including secretory breast cancer, colorectal cancer, prostate cancer including hormone refractory prostate cancer, bladder cancer, melanoma, lung cancer—non small cell lung cancer (NSCLC), and small cell lung cancer (SCLC), gastric cancer, head and neck cancer, renal cancer, lymphoma, thyroid cancer including papillary thyroid cancer, mesothelioma and leukaemia; particularly ovarian cancer, breast cancer, colorectal cancer, prostate cancer and lung cancer—NSCLC and SCLC; more particularly prostate cancer; and more particularly hormone refractory prostate cancer.

DETAILED DESCRIPTION OF THE INVENTION

Accordingly, the present invention provides a compound of formula (I):

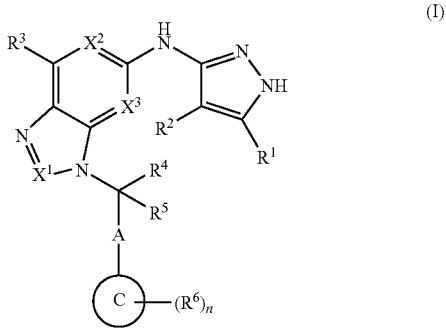

wherein:

R¹ and R² are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein R¹ and R² independently of each other may be optionally substituted on carbon by one or more R⁷; and wherein if said heterocyclyl contains an —NH— moiety that nitrogen may be optionally substituted by a group selected from R⁸;

X¹, X² and X³ are independently =N— or =CR⁹—;

R³ and R⁹ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl-R¹⁰— or heterocyclyl-R¹¹—; wherein R³ and R⁹ independently of each other may be optionally substituted on carbon by one or more R²; and wherein if said heterocyclyl contains an —NH— moiety that nitrogen may be optionally substituted by a group selected from R¹³;

R⁴ and R⁵ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein R⁴ and R⁵ independently of each other may be optionally substituted on carbon by one or more R¹⁴; and wherein if said heterocyclyl contains an —NH— moiety that nitrogen may be optionally substituted by a group selected from R¹⁵;

A is a direct bond or $C_{1-2}$alkylene; wherein said $C_{1-2}$alkylene may be optionally substituted by one or more R¹⁶;

Ring C is carbocyclyl or heterocyclyl; wherein if said heterocyclyl contains an —NH— moiety that nitrogen may be optionally substituted by a group selected from R¹⁷;

R⁶ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein R⁶ may be optionally substituted on carbon by one or more R¹⁸; and wherein if said heterocyclyl contains an —NH— moiety that nitrogen may be optionally substituted by a group selected from R¹⁹;

n is 0, 1, 2 or 3; wherein the values of R⁶ may be the same or different;

R⁷, R¹², R¹⁴, R¹⁶ and R¹⁸ and are independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl-R²⁰— or heterocyclyl-R²¹—; wherein R⁷, R¹², R¹⁴, R¹⁶ and R¹⁸ independently of each other may be optionally substituted on carbon by one or more R²²; and wherein if said heterocyclyl contains an —NH— moiety that nitrogen may be optionally substituted by a group selected from R²³;

R⁸, R¹³, R¹⁵, R¹⁷, R¹⁹ and R²³ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein R⁸, R¹³, R¹⁵, R¹⁷, R¹⁹ and R²³ independently of each other may be optionally substituted on carbon by on or more R²⁴;

R²² and R²⁴ are independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein R²² and R²⁴ independently of each other may be optionally substituted on carbon by one or more R²⁵; and wherein if said heterocyclyl contains an —NH-moiety that nitrogen may be optionally substituted by a group selected from R²⁶;

R¹⁰, R¹¹, R²⁰ and R²¹ are independently selected from a direct bond, —O—, —N(R²⁷)—, —C(O)—, —N(R²⁸)C(O)—, —C(O)N(R²⁹)—, —S(O)$_s$—, —SO$_2$N(R³⁰)— or —N(R³¹)SO$_2$—; wherein R²⁷, R²⁸, R²⁹, R³⁰ and R³¹ are independently selected from hydrogen or $C_{1-6}$alkyl and s is 0-2;

R²⁵ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{26}$ is selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

or a pharmaceutically acceptable salt thereof.

Particular values of the variable groups contained in formula (I) are as follows. Such values may be used, where appropriate, with any of the definitions, claims or embodiments defined hereinbefore or hereinafter.

$R^1$ is selected from $C_{1-6}$alkyl, $C_{1-6}$alkoxy or carbocyclyl.

$R^1$ is selected from methyl, t-butyl, isopropoxy or cyclopropyl.

$R^2$ is hydrogen.

$R^1$ and $R^2$ are independently selected from hydrogen, $C_{1-6}$alkyl, $C_{1-6}$alkoxy or carbocyclyl.

$R^1$ and $R^2$ are independently selected from hydrogen, methyl, t-butyl, isopropoxy or cyclopropyl.

$X^3$ is —N—; and $X^1$ and $X^2$ are independently =$CR^9$—.

$X^1$, $X^2$ and $X^3$ are independently =$CR^9$—.

$X^1$ is =$CR^9$—; and $X^2$ and $X^3$ are =N—.

$X^2$ is =$CR^9$—; and $X^1$ and $X^3$ are =N—.

$R^3$ and $R^9$ are independently selected from hydrogen, halo, hydroxy and $C_{1-6}$alkyl.

$R^3$ and $R^9$ are independently selected from hydrogen, fluoro, chloro, hydroxy and methyl.

$R^4$ and $R^5$ are independently selected from hydrogen or $C_{1-6}$alkyl; wherein $R^4$ and $R^5$ independently of each other may be optionally substituted on carbon by one or more $R^{14}$; wherein $R^{14}$ is hydroxy.

$R^4$ and $R^5$ are independently selected from hydrogen or methyl; wherein $R^4$ and $R^5$ independently of each other may be optionally substituted on carbon by one or more $R^{14}$; wherein $R^{14}$ is hydroxy.

$R^4$ and $R^5$ are independently selected from hydrogen, methyl or hydroxymethyl.

A is a direct bond.

A is $C_{1-2}$alkylene; wherein said $C_{1-2}$alkylene may be optionally substituted by one or more $R^{16}$.

Ring C is heterocyclyl; wherein if said heterocyclyl contains an —NH— moiety that nitrogen may be optionally substituted by a group selected from $R^{17}$.

Ring C is carbocyclyl.

Ring C is phenyl.

Ring C is phenyl, pyridyl, pyrimidinyl, 1,3-benzodioxolyl or 1H-indolyl.

Ring C is phenyl, pyrid-2-yl, pyrimidin-2-yl, 1,3-benzodioxol-5-yl or 1H-indol-3-yl.

Ring C is pyridyl.

Ring C is pyrid-2-yl.

Ring C is pyrimidinyl.

Ring C is pyrimidin-2-yl.

$R^6$ is halo.

$R^6$ is fluoro.

n is 0 or 1.

n is 1.

Ring C, $R^6$ and n together form 4-fluorophenyl, 5-fluoropyrid-2-yl or 5-fluoropyrimidin-2-yl.

Ring C, $R^6$ and n together form 4-fluorophenyl.

Ring C, $R^6$ and n together form 5-fluoropyrid-2-yl.

Ring C, $R^6$ and n together form 5-fluoropyrimidin-2-yl.

Therefore in a further aspect of the invention there is provided a compound of formula (I) (as depicted herein above) wherein:

$R^1$ and $R^2$ are independently selected from hydrogen, $C_{1-6}$alkyl, $C_{1-6}$alkoxy or carbocyclyl;

$X^1$, $X^2$ and $X^3$ are independently =N— or =$CR^9$—;

$R^3$ and $R^9$ are independently selected from hydrogen, halo, hydroxy and $C_{1-6}$alkyl;

$R^4$ and $R^5$ are independently selected from hydrogen or $C_{1-6}$alkyl; wherein $R^4$ and $R^5$ independently of each other may be optionally substituted on carbon by one or more $R^{14}$;

A is a direct bond;

Ring C is carbocyclyl;

$R^6$ is halo;

n is 1; and $R^{14}$ is hydroxy;

or a pharmaceutically acceptable salt thereof.

Therefore in a further aspect of the invention there is provided a compound of formula (I) (as depicted herein above) wherein:

$R^1$ is selected from methyl, t-butyl, isopropoxy or cyclopropyl;

$R^2$ is hydrogen;

$X^1$, $X^2$ and $X^3$ are independently =N— or =$CR^9$—;

$R^3$ and $R^9$ are independently selected from hydrogen, fluoro, chloro, hydroxy and methyl;

$R^4$ and $R^5$ are independently selected from hydrogen, methyl or hydroxymethyl;

A is a direct bond;

Ring C is phenyl;

$R^6$ is fluoro; and n is 1;

or a pharmaceutically acceptable salt thereof.

In another aspect of the invention, preferred compounds of the invention are any one of the Examples or a pharmaceutically acceptable salt thereof.

In a further aspect of the invention there is provided a compound of formula (I) selected from Examples 6, 11, 14, 15, 16, 24, 26, 27, 28 or 30 or a pharmaceutically acceptable salt thereof.

In an additional embodiment the present invention provides a compound of formula (I), or a pharmaceutically acceptable salt thereof, for use as a medicament.

In an additional embodiment the present invention provides a compound of formula (I), or a pharmaceutically acceptable salt thereof, for use in the manufacture of a medicament for use in the inhibition of Trk activity.

In an additional embodiment the present invention provides a compound of formula (I), or a pharmaceutically acceptable salt thereof, for use in the manufacture of a medicament for use in the treatment or prophylaxis of cancer.

In an additional embodiment the present invention provides a compound of the formula (I), or a pharmaceutically acceptable salt thereof, for use in the manufacture of a medicament for use in the treatment of cancer in a warm-blooded animal such as man.

In an additional embodiment the present invention provides a compound of the formula (I), or a pharmaceutically acceptable salt thereof, for use in the manufacture of a medicament for use in the treatment or prophylaxis of cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation in a warm-blooded animal such as man.

In an additional embodiment the present invention provides a compound of formula (I), or a pharmaceutically acceptable salt thereof, for use in the manufacture of a medicament for use in the production of an anti-proliferative effect.

In an additional embodiment the present invention provides a method of inhibiting Trk activity comprising administering to a host in need of such treatment a therapeutically effective amount of a compound of formula (I), or a pharmaceutically acceptable salt thereof.

In an additional embodiment the present invention provides a method for the treatment of cancer comprising administering to a host in need of such treatment a therapeutically effective amount of a compound of formula (I), or a pharmaceutically acceptable salt thereof.

In an additional embodiment the present invention provides a method for the treatment or prophylaxis of cancer comprising administering a therapeutically effective amount of a compound of formula (I) or a pharmaceutically acceptable salt thereof.

In an additional embodiment the present invention provides a method for the treatment or prophylaxis of cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation in a warm-blooded animal such as man comprising administering a therapeutically effective amount of a compound of formula (I) or a pharmaceutically acceptable salt thereof.

In an additional embodiment the present invention provides a method of producing an anti-proliferative effect in a warm-blooded animal, such as man, in need of such treatment which comprises administering to said animal an effective amount of a compound of formula (I), or a pharmaceutically acceptable salt thereof.

In an additional embodiment the present invention provides a pharmaceutical composition comprising a compound of formula (I), or a pharmaceutically acceptable salt thereof, together with at least one pharmaceutically acceptable carrier, diluent or excipient.

In an additional embodiment the present invention provides a pharmaceutical composition comprising a compound of formula (I), or a pharmaceutically acceptable salt thereof, together with at least one pharmaceutically acceptable carrier, diluent or excipient for use in the inhibition of Trk activity.

In an additional embodiment the present invention provides a pharmaceutical composition comprising a compound of formula (I), or a pharmaceutically acceptable salt thereof, together with at least one pharmaceutically acceptable carrier, diluent or excipient for use in the treatment of cancer.

In an additional embodiment the present invention provides a pharmaceutical composition comprising a compound of formula (I), or a pharmaceutically acceptable salt thereof, together with at least one pharmaceutically acceptable carrier, diluent or excipient for use in the treatment or prophylaxis of cancer.

In an additional embodiment the present invention provides a pharmaceutical composition comprising a compound of formula (I), or a pharmaceutically acceptable salt thereof, together with at least one pharmaceutically acceptable carrier, diluent or excipient for use in the treatment or prophylaxis of cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

In an additional embodiment the present invention provides a pharmaceutical composition comprising a compound of formula (I), or a pharmaceutically acceptable salt thereof, together with at least one pharmaceutically acceptable carrier, diluent or excipient for use in the production of an anti-proliferative effect in a warm-blooded animal such as man.

In an additional embodiment the present invention provides a compound of formula (I), or a pharmaceutically acceptable salt thereof, for use in the inhibition of Trk activity.

In an additional embodiment the present invention provides a compound of formula (I), or a pharmaceutically acceptable salt thereof, for use in the treatment or prophylaxis of cancer.

In an additional embodiment the present invention provides a compound of the formula (I), or a pharmaceutically acceptable salt thereof, for use in the treatment of cancer in a warm-blooded animal such as man.

In an additional embodiment the present invention provides a compound of the formula (I), or a pharmaceutically acceptable salt thereof, for use in the treatment or prophylaxis of cancers (solid tumours and leukaemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation in a warm-blooded animal such as man.

In an additional embodiment the present invention provides a compound of formula (I), or a pharmaceutically acceptable salt thereof, for use in the production of an anti-proliferative effect.

In one embodiment where the inhibition of Trk activity is referred to particularly this refers to the inhibition of Trk A activity.

In another embodiment where the inhibition of Trk activity is referred to particularly this refers to the inhibition of Trk B activity.

Where the treatment (or prophylaxis) of cancer is referred to, particularly it refers to the treatment (or prophylaxis) of congenital fibrosarcoma, mesoblastic nephroma, mesothelioma, acute myeloblastic leukemia, acute lymphocytic leukemia, multiple myeloma, melanoma, oesophageal cancer, myeloma, hepatocellular, pancreatic, cervical cancer, Ewings sarcoma, neuroblastoma, Kaposis sarcoma, ovarian cancer, breast cancer including secretory breast cancer, colorectal cancer, prostate cancer including hormone refractory prostate cancer, bladder cancer, melanoma, lung cancer—non small cell lung cancer (NSCLC), and small cell lung cancer (SCLC), gastric cancer, head and neck cancer, renal cancer, lymphoma, thyroid cancer including papillary thyroid cancer, mesothelioma, leukaemia, tumours of the central and peripheral nervous system, melanoma, fibrosarcoma including congenital fibrosarcoma and osteosarcoma. More particularly it refers to prostate cancer. In addition, more particularly it refers to SCLC, NSCLC, colorectal cancer, ovarian cancer and/or breast cancer. In a further aspect it refers to hormone refractory prostate cancer.

In a further aspect of the present invention provides a process for preparing a compound of formula (I) or a pharmaceutically acceptable salt thereof which process (wherein variable groups are, unless otherwise specified, as defined in formula (I)) comprises of:

Process a) reaction of a compound of formula (II):

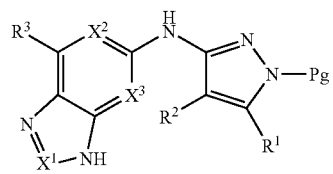

(II)

wherein Pg is a nitrogen protecting group; with a compound of formula (III):

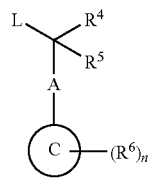

(III)

wherein L is a displaceable group;

Process b) for compounds of formula (I) wherein $R^4$ is hydroxymethyl and $R^5$ is hydrogen; reaction of a compound of formula (II) with an epoxide of formula (IV):

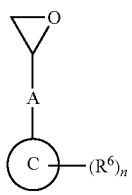

(IV)

Process c) for compounds of formula (I) wherein $X^1$ is $=CR^9-$; reacting a compound of formula (V):

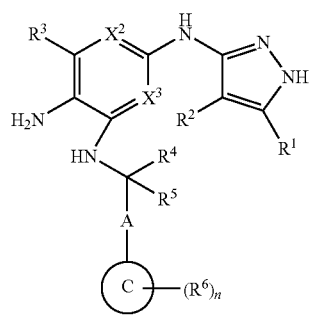

(V)

with a compound of formula (VI):

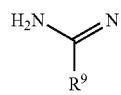

(VI)

Process d) for compounds of formula (I) wherein $X^1$ is $=N-$; reacting a compound of formula (V) with aqueous $NaNO_2$ solution;

Process e) reacting a compound of formula (VII):

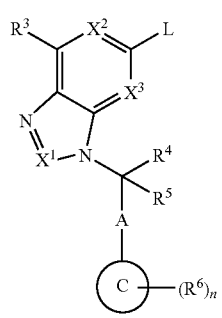

(VII)

wherein L is a displaceable group; with an amine of formula (VIII):

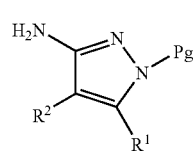

(VIII)

wherein Pg is a nitrogen protecting group;

Process f) reacting a compound of formula (IX):

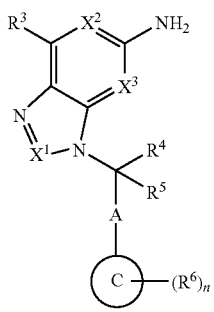

(IX)

with a compound of formula (X):

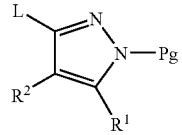

wherein L is a displaceable group;

and thereafter if necessary:

i) converting a compound of the formula (I) into another compound of the formula (I);

ii) removing any protecting groups;

iii) forming a pharmaceutically acceptable salt.

L is a displaceable group, suitable values for L are for example, a halo or sulphonyloxy group, for example a chloro, bromo, methanesulphonyloxy or toluene-4-sulphonyloxy group.

Pg is a nitrogen protecting group. Suitable values for Pg are described herein below.

Specific reaction conditions for the above reactions are as follows.

Process a) Compounds of formula (II) and (III) may be reacted together under standard nucleophilic addition reactions for example in the presence of a suitable base such as potassium carbonate and a suitable solvent such as DMF and at a temperature in the range from 25 to 10° C.

Compounds of the formula (II) may be prepared according to Scheme 1:

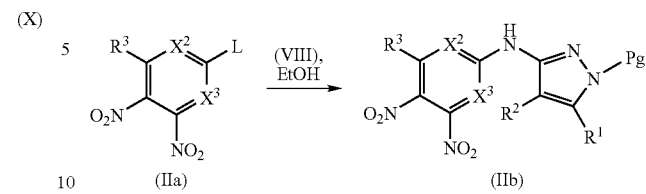

wherein L is a displaceable group as defined herein above.

Compounds of formula (III) and (IIa) are commercially available compounds, or they are known in the literature, or they are prepared by standard processes known in the art.

Process b) Compounds of formula (II) and (IV) may be reacted together under epoxide ring opening reaction conditions for example in the presence of a suitable catalyst such as LiClO$_4$, NaClO$_4$, Mg(ClO$_4$)$_2$ and a suitable solvent such as CH$_3$CN and at a temperature in the range from 25 to 80° C.

Compounds of formula (IV) are commercially available compounds, or they are known in the literature, or they are prepared by standard processes known in the art.

Process c) Compounds of formula (V) and compounds of formula (VI) may be reacted together in a suitable solvent such as ethanol at reflux temperature.

Compounds (V) may be prepared according to Scheme 2:

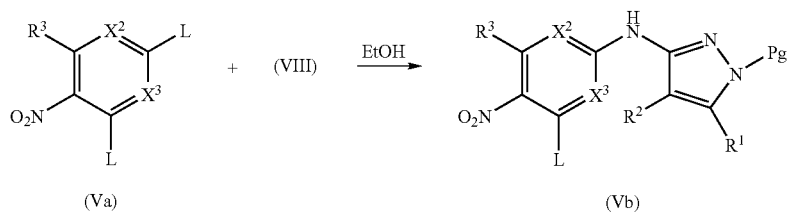

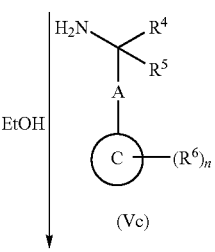

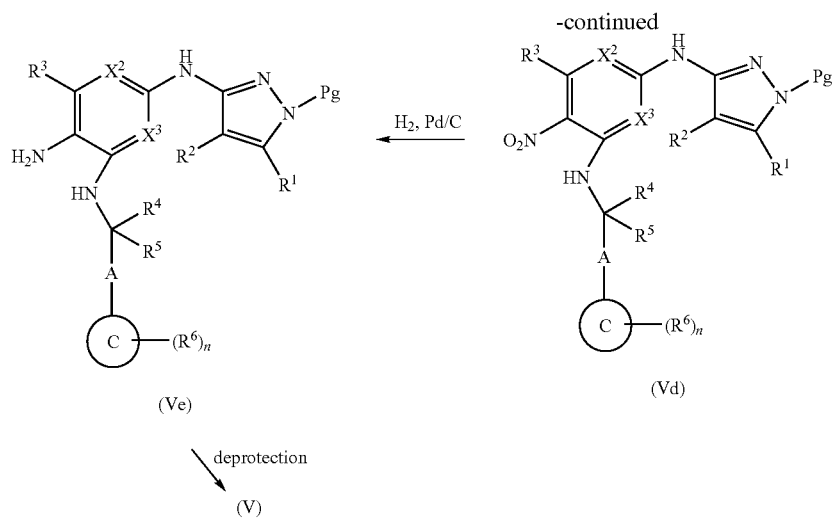

wherein L is a displaceable group and Pg is a nitrogen protecting group as defined herein above.

Compounds of formula (Va), (Vc) and (VI) are commercially available compounds, or they are known in the literature, or they are prepared by standard processes known in the art.

Process d) Compounds of formula (V) and an aqueous $NaNO_2$ solution may be reacted together in aqueous acetic acid.

Process e) Compounds of formula (VII) and (VIII) may be reacted together under the conditions listed in Process a).

Compounds of formula (VII) wherein $X^1$ is selected from $=CR^9-$ may be prepared according to Scheme 3:

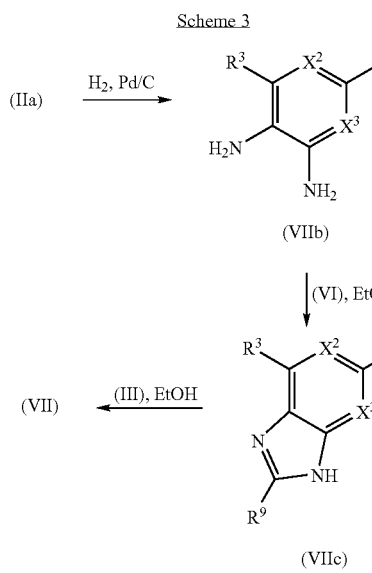

wherein L is a displaceable group as defined herein above.

Compounds of formula (VII) wherein $X^1$ is selected from $=CR^9-$ and $R^9$ is hydroxy may be prepared according to Scheme 4:

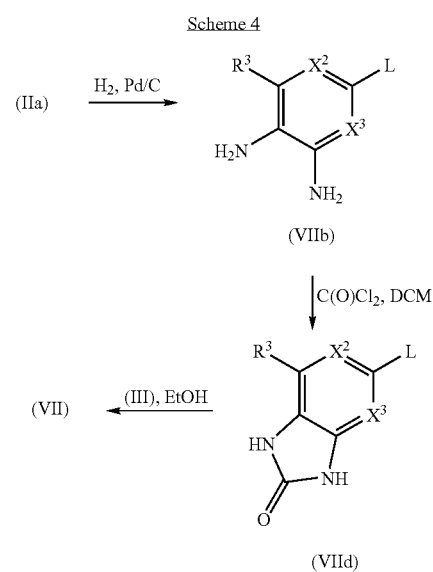

wherein L is a displaceable group as defined herein above.

Compounds of formula (VII) wherein $X^1$ is selected from $=N-$ may be prepared according to Scheme 5:

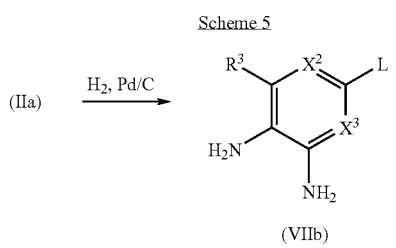

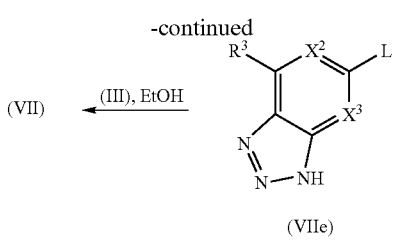

wherein L is a displaceable group as defined herein above.

Compounds of the formula (VIII) are commercially available compounds, or they are known in the literature, or they are prepared by standard processes known in the art.

Process f) Compounds of formula (IX) and (X) may be reacted together under the conditions listed in Process a).

Compounds of formula (IX) may be prepared according to Scheme 6:

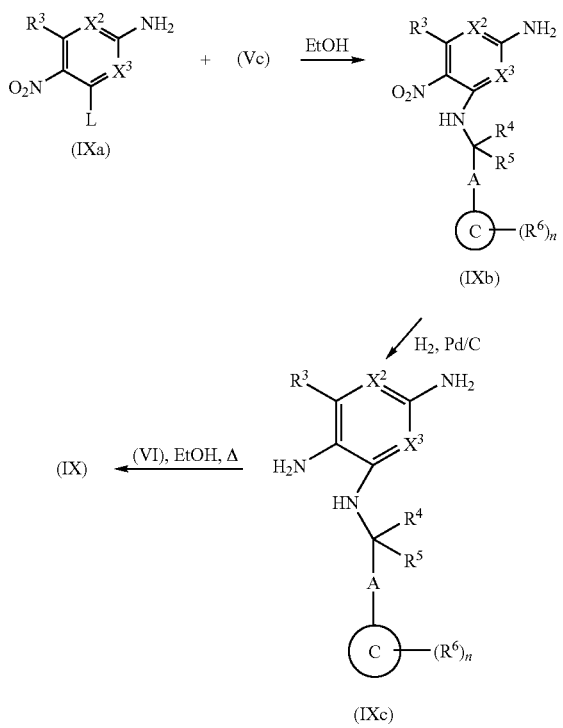

wherein L is a displaceable group as defined herein above.

Compounds of the formula (IXa) and (X) are commercially available compounds, or they are known in the literature, or they are prepared by standard processes known in the art.

Certain intermediates disclosed herein are novel as such they are provided as a further feature of the invention.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

DEFINITIONS

In this specification the term "alkyl" includes both straight and branched chain alkyl groups but references to individual alkyl groups such as "propyl" are specific for the straight chain version only. For example, "$C_{1-6}$alkyl" and "$C_{1-4}$alkyl" include methyl, ethyl, propyl, isopropyl and t-butyl. However, references to individual alkyl groups such as 'propyl' are specific for the straight-chained version only and references to individual branched chain alkyl groups such as 'isopropyl' are specific for the branched-chain version only. A similar convention applies to other radicals. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclyl" is a saturated, partially saturated or unsaturated, mono or bicyclic ring containing 4-12 atoms of which at least one atom is chosen from nitrogen, sulphur or oxygen, which may, unless otherwise specified, be carbon or nitrogen linked, wherein a —$CH_2$— group can optionally be replaced by a —C(O)—, and a ring sulphur atom may be optionally oxidised to form the S-oxides. Examples and suitable values of the term "heterocyclyl" are morpholino, piperidyl, pyridyl, pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone, 4-thiazolidone, pyridine-N-oxide and quinoline-N-oxide. Further examples and suitable values of the term "heterocyclyl" are morpholino, piperazinyl and pyrrolidinyl. In one aspect of the invention a "heterocyclyl" is a saturated, partially saturated or unsaturated, mono or bicyclic ring containing 5 or 6 atoms of which at least one atom is chosen from nitrogen, sulphur or oxygen, it may, unless otherwise specified, be carbon or nitrogen linked, a —$CH_2$— group can optionally be replaced by a —C(O)— and a ring sulphur atom may be optionally oxidised to form the S-oxides.

A "carbocyclyl" is a saturated, partially saturated or unsaturated, mono or bicyclic carbon ring that contains 3-12 atoms; wherein a —$CH_2$— group can optionally be replaced by a —C(O)—. Particularly "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl.

The term "$C_{m-n}$" or "$C_{m-n}$ group" used alone or as a prefix, refers to any group having m to n carbon atoms.

The term "optionally substituted" refers to either groups, structures, or molecules that are substituted and those that are not substituted.

An example of "$C_{1-6}$alkanoyloxy" is acetoxy. Examples of "$C_{1-6}$alkoxycarbonyl" include $C_{1-4}$alkoxycarbonyl, methoxycarbonyl, ethoxycarbonyl, n- and t-butoxycarbonyl. Examples of "$C_{1-6}$alkoxy" include $C_{1-4}$alkoxy, $C_{1-3}$alkoxy, methoxy, ethoxy and propoxy. Examples of "$C_{1-6}$alkoxyimino" include $C_{1-4}$alkoxyimino, $C_{1-3}$alkoxyimino, methoxyimino, ethoxyimino and propoxyimino. Examples of "$C_{1-6}$alkanoylamino" include formamido, acetamido and propionylamino. Examples of "$C_{1-6}$alkylS(O)$_a$ wherein a is 0 to 2" include $C_{1-4}$alkylsulphonyl, methylthio, ethylthio, methylsulphinyl, ethylsulphinyl, mesyl and ethylsulphonyl. Examples of "$C_{1-6}$alkylthio" include methylthio and ethylthio. Examples of "$C_{1-6}$alkylsulphonylamino" include methylsulphonylamino and ethylsulphsulphonylamino. Examples of "$C_{1-6}$alkanoyl" include $C_{1-4}$alkanoyl, propionyl and acetyl. Examples of "N—($C_{1-6}$alkyl)amino" include methylamino and ethylamino. Examples of "N,N—($C_{1-6}$alkyl)$_2$amino" include di-N-methylamino, di-(N-ethyl)amino and N-ethyl-N-methylamino. Examples of "$C_{2-6}$alkenyl" are vinyl, allyl and 1-propenyl. Examples of "$C_{2-6}$alkynyl" are ethynyl, 1-propynyl and 2-propynyl. Examples of "N—($C_{1-6}$alkyl)sulphamoyl" are N-(methyl)sulphamoyl and N-(ethyl)sulphamoyl. Examples of "N—($C_{1-6}$alkyl)$_2$sulphamoyl" are N,N-(dimethyl)sulphamoyl and N-(methyl)-N-(ethyl)sulphamoyl. Examples of "N—($C_{1-6}$alkyl)carbamoyl" are N—($C_{1-4}$alkyl)carbamoyl, methylaminocarbonyl and ethylaminocarbonyl. Examples of "N,N—($C_{1-6}$alkyl)$_2$carbamoyl" are N,N—($C_{1-4}$alkyl)$_2$carbamoyl, dimethylaminocarbonyl and methylethylaminocarbonyl.

"RT" or "rt" means room temperature.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

It should be noted that the compounds claimed in this invention are capable of existing in different resonance structures and thus the compounds claimed herein include all possible resonance structures, for example optical isomers, diastereoisomers and geometric isomers and all tautomeric forms of the compounds of the formula (I).

It is also to be understood that certain compounds of the formula (I) can exist in solvated as well as unsolvated forms such as, for example, hydrated forms. It is to be understood that the invention encompasses all such solvated forms.

Formulations

Compounds of the present invention may be administered orally, parenteral, buccal, vaginal, rectal, inhalation, insufflation, sublingually, intramuscularly, subcutaneously, topically, intranasally, intraperitoneally, intrathoracially, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

An effective amount of a compound of the present invention for use in therapy of cancer is an amount sufficient to symptomatically relieve in a warm-blooded animal, particularly a human the symptoms of cancer, to slow the progression of cancer, or to reduce in patients with symptoms of cancer the risk of getting worse.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substance, which may also act as diluents, flavoring agents, solubilizers, lubricants, suspending agents, binders, or tablet disintegrating agents; it can also be an encapsulating material.

In powders, the carrier is a finely divided solid, which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers include magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Some of the compounds of the present invention are capable of forming salts with various inorganic and organic acids and bases and such salts are also within the scope of this invention. Examples of such acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Base salts include ammonium salts, alkali metal salts such as sodium, lithium and potassium salts, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates like dimethyl, diethyl, dibutyl; diamyl sulfates; long chain halides such as decyl, lauryl, myristyl and stearyl halides; aralkyl halides like benzyl bromide and others. Nontoxic physiologically-acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

In order to use a compound of the formula (I) or a pharmaceutically acceptable salt thereof for the therapeutic treatment (including prophylactic treatment) of mammals including humans, it is normally formulated in accordance with standard pharmaceutical practice as a pharmaceutical composition.

In addition to the compounds of the present invention, the pharmaceutical composition of this invention may also contain, or be co-administered (simultaneously or sequentially) with, one or more pharmacological agents of value in treating one or more disease conditions referred to herein.

The term composition is intended to include the formulation of the active component or a pharmaceutically acceptable salt with a pharmaceutically acceptable carrier. For example this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Combinations

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD 1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin $\alpha_v\beta_3$ function and angiostatin);

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies; and (x) other treatment regimes including: dexamethasone, proteasome inhibitors (including bortezomib), isotretinoin (13-cis retinoic acid), thalidomide, revemid, Rituxamab, ALIMTA, Cephalon's kinase inhibitors CEP-701 and CEP-2563, anti-Trk or anti-NGF monoclonal antibodies, targeted radiation therapy with 131I-metaiodobenzylguanidine (131I-MIBG), anti-G(D2) monoclonal antibody therapy with or without granulocyte-macrophage colony-stimulating factor (GM-CSF) following chemotherapy.

Such conjoint treatment may be achieved by way of the simultaneous, sequential or separate dosing of the individual components of the treatment. Such combination products employ the compounds of this invention, or pharmaceutically acceptable salts thereof, within the dosage range described hereinbefore and the other pharmaceutically-active agent within its approved dosage range.

Synthesis

The compounds, or pharmaceutically acceptable salts thereof, of the present invention can be prepared in a number of ways well known to one skilled in the art of organic synthesis. The compounds, or pharmaceutically acceptable salts thereof, of the present invention can be synthesized using the methods described below, together with synthetic methods known in the art of synthetic organic chemistry, or variations thereon as appreciated by those skilled in the art. Such methods include, but are not limited to, those described below. All references cited herein are hereby incorporated in their entirety by reference.

The novel compounds, or pharmaceutically acceptable salts thereof, of this invention may be prepared using the reactions and techniques described herein. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used.

EXAMPLES

The invention will now be further described with reference to the following illustrative examples in which, unless stated otherwise:

(i) temperatures are given in degrees Celsius (° C.); operations are carried out at room temperature or ambient temperature, that is, in a range of 18-25° C.;

(ii) organic solutions were dried over anhydrous magnesium sulfate; evaporation of organic solvent was carried out using a rotary evaporator under reduced pressure (4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC or liquid chromatography/mass spectroscopy (LC/MS) and reaction times are given for illustration only;

(v) final products have satisfactory proton nuclear magnetic resonance (NMR) spectra and/or mass spectra data;

(vi) yields are given for illustration only and are not necessarily those which can be obtained by diligent process development; preparations were repeated if more material was required;

(vii) when given, NMR data is in the form of delta values for major diagnostic protons, given in part per million (ppm) relative to tetramethylsilane (TMS) as an internal standard, determined at 300 MHz in DMSO-$d_6$ unless otherwise stated;
(viii) chemical symbols have their usual meanings;
(ix) solvent ratio was given in volume:volume (v/v) terms.
(x) the following abbreviations have been used:
  EtOAc ethyl acetate;
  EtOH ethanol;
  THF tetrahydrofuran;
  DIEA diisopropylethylamine
  DPPA diphenyl phosphorazidate;
  MeOH methanol; and
  DCM dichloromethane.

Example 1

(2R)-2-{2-[(5-Cyclopropyl-1H-pyrazol-3-yl)amino]-9H-purin-9-yl}-2-(4-fluorophenyl)ethanol To a 25 ml round bottom flask was added palladium on activated carbon (10%, 104 mg, 0.098 mmol) and stirring bar. The flask was sealed, evacuated and refilled with hydrogen using balloon. A solution of (2R)-2-({2-[(5-cyclopropyl-1H-pyrazol-3-yl)amino]-5-nitropyrimidin-4-yl}amino)-2-(4-fluorophenyl)ethanol (Method 1, 196 mg, 0.49 mmol) in EtOH/EtOAc (6 ml/1 ml) via syringe. The reaction mixture was stirred at room temperature for 19 hours and was filtered through paper. The filtrate was concentrated to give a pink solid. The solid was then dissolved in EtOH (4 ml) and to the mixture was added formamidine acetate (100 mg, 0.96 mmol). The reaction mixture was heated on heating block (70° C.) for 4 hours. Removal of solvent followed by flash chromatography on silica gel (10-15% MeOH in EtOAc) gave the desired product as a solid (114 mg, 61% for two steps). NMR: 0.63 (m, 2H), 0.93 (m, 2H), 1.86 (m, 1H), 4.04 (m, 1H), 4.38 (m, 1H), 5.34 (m, 1H), 5.70 (m, 1H), 6.20 (m, 1H), 7.18 (m, 2H), 7.45 (m, 2H), 8.45 (s, 1H), 8.73 (s, 1H), 9.48 (br s, 1H), 11.85 (br s, 1H).

Examples 2-5

Following a similar procedure to Example 1, the following compounds were synthesized from a suitable pyrimidine by reacting it sequentially with $H_2$ and formamidine acetate.

Example 6

(S)—N-(5-Cyclopronyl-1H-pyrazol-3-yl)-3-(1-(4-fluorophenyl)ethyl)-3H-imidazo[4,5-b]pyridin-5-amine A mixture of (S)—$N^6$-(5-cyclopropyl-1H-pyrazol-3-yl)-$N^2$-(1-(4-fluorophenyl)ethyl)pyridine-2,3,6-triamine (Method 9; 0.260 g, 0.74 mmol) and formamidine acetate (0.123 g, 1.18 mmol) in EtOH (5 ml) was heated at reflux overnight. After cooling to 25° C., saturated $NaHCO_3$ solution (10 ml) and EtOAc (30 ml) were added to the reaction mixture. The organic layer was separated, washed with brine (10 ml), dried over $Na_2SO_4$, concentrated, and purified by column chromatography (EtOAc:MeOH=40:1) to give the title compound as an off-white solid (0.135 g, 50%). NMR (400 MHz) 11.78 (s, 1H), 9.23 (s, 1H), 8.29 (s, 1H), 7.76 (d, J=8.8 Hz, 1H), 7.38 (m, 2H), 7.16 (m, 2H), 6.90 (d, J=8.8 Hz, 1H), 6.21 (s, 1H), 5.84 (m, 1H), 1.95 (d, J=7.2 Hz, 3H), 1.86 (m, 1H), 0.94 (m, 2H), 0.65 (m, 2H). MS: Calcd.: 362. Found: [M+H]$^+$ 363.

Example 7

(S)-5-(5-Cyclopropyl-1H-pyrazol-3-ylamino)-3-(1-(4-fluorophenyl)ethyl-1H-imidazo[4,5-b]pyridin-2(3H)-one A mixture of crude (S)—$N^6$-(5-cyclopropyl-1H-pyrazol-3-yl)-$N^2$-(1-(4-fluorophenyl)ethyl)pyridine-2,3,6-triamine (Method 9; 0.100 g, 0.28 mmol) and carbodiimidazole (0.092 g, 0.57 mmol) in THF (5 ml) was stirred at 25° C. for 2 hours. The solvent was removed under reduced pressure and the residue was purified by column chromatography (EtOAc) to give the title compound as a white solid (0.083 g, 77%). NMR (400 MHz) 11.68 (s, 1H), 10.68 (s, 1H), 8.79 (br s, 1H), 7.45 (m, 2H), 7.14 (m, 3H), 6.78 (d, J=8.8 Hz, 1H), 5.85 (s, 1H), 5.63 (m, 1H), 1.94 (d, J=7.2 Hz, 3H), 1.80 (m, 1H), 0.87 (m, 2H), 0.56 (m, 2H). MS: Calcd.: 378. Found: [M+H]$^+$ 379.

| Ex | Compound | NMR | SM |
|---|---|---|---|
| 2 | N-(5-Cyclopropyl-1H-pyrazol-3-yl)-9-(4-fluorobenzyl)-9H-purin-2-amine | 0.63 (m, 2H), 0.91 (m, 2H), 1.85 (m, 1H), 5.38 (s, 2H), 6.15 (s, 1H), 7.17 (m, 2H), 7.42 (m, 2H), 8.33 (s, 1H), 8.75 (s, 1H), 9.20 (br s, 1H) | Method 2 |
| 3 | (2R)-2-(4-Fluorophenyl)-2-{2-[(5-methyl-1H-pyrazol-3-yl)amino]-9H-purin-9-yl}ethanol | 2.21 (s, 3H), 4.08 (m, 1H), 4.37 (m, 1H), 5.37 (m, 1H), 5.69 (br s, 1H), 6.30 (s, 1H), 7.18 (m, 2H), 7.44 (m, 2H), 8.45 (s, 1H), 8.73 (s, 1H), 9.81 (br s, 1H), 11.81 (br s, 1H) | Method 3 |
| 4 | N-(5-Cyclopropyl-1H-pyrazol-3-yl)-9-[(1S)-1-(4-fluorophenyl)ethyl]-9H-purin-2-amine | 0.64 (m, 2H), 0.92 (m, 2H), 1.93 (m, 1H), 1.94 (m, 3H), 5.80 (s, 1H), 6.25 (s, 1H), 7.17 (m, 2H), 7.42 (m, 2H), 8.45 (s, 1H), 8.73 (s, 1H), 9.49 (br s, 1H), 11.87 (br s, 1H) | Method 4 |
| 5 | 9-[(1S)-1-(4-Fluorophenyl)ethyl]-N-(5-isopropoxy-1H-pyrazol-3-yl)-9H-purin-2-amine | 1.27 (m, 6H), 1.91 (m, 3H), 4.65 (m, 1H), 5.36 (s, 1H), 6.10 (s, 1H), 7.17 (m, 2H), 7.43 (m, 2H), 8.52 (s, 1H), 8.81 (s, 1H), 10.11 (br s, 1H), 11.21 (br s, 1H) | Method 5 |

Example 8

(S)—N-(5-Cyclopropyl-1H-pyrazol-3-yl)-3-(1-(4-fluorophenyl)ethyl)-2-methyl-3H imidazo[4,5-b]pyridin-5-amine A mixture of crude (S)—N$^6$-(5-cyclopropyl-1H-pyrazol-3-yl)-N$^2$-(1-(4-fluorophenyl)ethyl)pyridine-2,3,6-triamine (Method 9; 0.120 g, 0.34 mmol) and acetamidine hydrochloride (0.052 g, 0.55 mmol) in EtOH (5 ml) was heated at reflux overnight. After cooling to 25° C., saturated NaHCO$_3$ solution (10 ml) and EtOAc (30 ml) were added to the reaction mixture. The organic layer was separated, washed with brine (10 ml), dried over Na$_2$SO$_4$, concentrated, and purified by chromatography (EtOAc:MeOH=100:1) to give the title compound as an off-white solid (0.055 g, 43%). NMR (400 MHz, d$^6$-Acetone) 11.14 (br s, 1H), 8.44 (br s, 1H), 7.70 (d, J=8.4 Hz, 1H), 7.44 (m, 2H), 7.11 (m, 2H), 7.00 (br s, 1H), 6.00 (m, 2H), 2.12 (s, 3H), 2.11 (d, J=7.2 Hz, 3H), 0.89 (m, 2H), 0.65 (m, 2H). MS: Calcd.: 376. Found: [M+H]$^+$ 377.

Example 9-13

Following a similar procedure to Example 6 (or Example 8-Example 10), the following compounds were synthesized from a suitable pyridine by reacting it with formamidine acetate (or acetamidine hydrochloride in Example 10).

Example 14

(S)-6-Chloro-N-(5-cyclopropyl-1H-pyrazol-3-yl)-3-(1-(4-fluorophenyl)ethyl)-3H-imidazo[4,5-b]pyridin-5-amine A mixture of (S)-5-chloro-N$^6$-(5-cyclopropyl-1H-pyrazol-3-yl)-N$^2$-(1-(4-fluorophenyl)ethyl)pyridine-2,3,6-triamine (Method 27; 0.300 g, 0.77 mmol) and formamidine acetate (0.129 g, 1.24 mmol) in EtOH (5 ml) was heated at reflux overnight. After cooling to 25° C., the reaction mixture was treated with saturated NaHCO$_3$ (10 ml) and EtOAc (30 ml). The organic layer was separated, washed with brine (10 ml), and dried over Na$_2$SO$_4$. The solvent was removed under reduced pressure and the residue was purified by column chromatography (EtOAc:MeOH=20:1) to give the title compound as an off-white solid (0.145 g, 47%). NMR (400 MHz) 11.96 (br s, 1H), 8.45 (s, 1H), 8.13 (br s, 1H), 8.12 (s, 1H), 7.36 (m, 2H), 7.16 (m, 1H), 6.18 (s, 1H), 5.87 (br s, 1H), 1.95 (d, J=6.8 Hz, 3H), 1.90 (m, 1H), 0.95 (m, 2H), 0.66 (m, 2H). MS: Calcd.: 396. Found: [M+H]$^+$ 397.

Example 15-18

Following a similar procedure to Example 14, the following compounds were synthesized from a suitable aminopyridine by reacting it with formamidine acetate.

| Ex | Compound | NMR/MS | SM |
|---|---|---|---|
| 9 | 3-(4-Fluorobenzyl)-N-(5-cyclopropyl-1H-pyrazol-3-yl)-3H-imidazo[4,5-b]pyridin-5-amine | (400 MHz) 11.79 (s, 1H), 9.26 (s, 1H), 8.18 (s, 1H), 7.78 (d, J = 8.0 Hz, 1H), 7.38 (m, 2H), 7.17 (m, 2H), 6.93 (br s, 1H), 6.24 (s, 1H), 5.39 (s, 2H), 1.85 (m, 1H), 0.92 (m, 2H), 0.64 (m, 2H). MS: Calcd.: 348; Found: [M + H]$^+$ 349 | Method 10 |
| 10 | 3-(4-Fluorobenzyl)-N-(5-cyclopropyl-1H-pyrazol-3-yl)-2-methyl-3H-imidazo[4,5-b]pyridin-5-amine | (400 MHz) 11.74 (br s, 1H), 9.16 (br s, 1H), 7.16 (br s, 1H), 7.29 (m, 2H), 7.16 (m, 2H), 6.95 (br s, 1H), 6.18 (br s, 1H), 5.38 (br s, 2H), 1.83 (m, 1H), 0.88 (m, 2H), 0.60 (m, 2H). MS: Calcd.: 362; Found: [M + H]$^+$ 363 | Method 10 |
| 11 | (R)-2-(5-(5-Cyclopropyl-1H-pyrazol-3-ylamino)-3H-imidazo[4,5-b]pyridin-3-yl)-2-(4-fluorophenyl)ethanol | (400 MHz) 11.79 (s, 1H), 9.24 (br s, 1H), 8.33 (s, 1H), 7.78 (br s, 1H), 7.40 (m, 2H), 7.19 (m, 2H), 6.89 (br s, 2H), 6.21 (s, 1H), 5.73 (br s, 1H), 5.30 (s, 1H), 4.37 (m, 1H), 4.12 (m, 1H), 1.87 (m, 1H), 0.94 (m, 2H), 0.65 (m, 2H). MS: Calcd.: 378; Found: [M + H]$^+$ 379 | Method 11 |
| 12 | 2-(5-[(5-Cyclopropyl-1H-pyrazol-3-yl)amino]-3H-imidazo[4,5-b]pyridin-3-yl)-2-(4-fluorophenyl)propane-1,3-diol | (400 MHz) 11.64 (s, 1H), 9.11 (s, 1H), 8.17 (s, 1H), 7.75 (d, J = 8.4 Hz, 1H), 7.10 (m, 4H), 6.74 (d, J = 8.0 Hz, 1H), 5.49 (s, 1H), 5.18 (br s, 2H), 4.39 (m, 4H), 1.75 (m, 1H), 0.89 (m, 2H), 0.53 (m, 2H). MS: Calcd.: 408; Found: [M + H]$^+$ 409 | Method 12 |
| 13 | (R)—N-(5-Cyclopropyl-1H-pyrazol-3-yl)-3-(1-(4-fluorophenyl)ethyl)-3H-imidazo[4,5-b]pyridin-5-amine | (400 MHz, CD$_3$OD) 8.22 (s, 1H), 7.79 (d, J = 8.8 Hz, 1H), 7.40-7.36 (m, 2H), 7.09-7.05 (m, 2H), 6.78 (d, J = 8.8 Hz, 1H), 5.94-5.89 (m, 1H), 2.00 (d, J = 7.0 Hz, 3H), 1.91-1.87 (m, 1H), 0.97-0.93 (m, 2H), 0.71-0.68 (m, 2H). MS: Calcd.: 362; Found: [M + H]$^+$ 363 | Method 13 |

| Ex | Compound | NMR/MS | SM |
|---|---|---|---|
| 15 | (R)-2-(6-Chloro-5-(5-cyclopropyl-1H-pyrazol-3-ylamino)-3H-imidazo[4,5-b]pyridin-3-yl)-2-(4-fluorophenyl)ethanol | (400 MHz) 12.03 (s, 1H), 8.45 (s, 1H), 8.11 (s, 1H), 8.03 (br s, 1H), 7.38 (m, 2H), 7.17 (m, 2H), 6.21 (s, 1H), 5.71 (br s, 1H), 5.29 (t, J = 5.2 Hz, 1H), 4.37 (m, 1H), 4.08 (m, 1H), 1.89 (m, 1H), 0.96 (m, 2H), 0.65 (m, 2H). MS: Calcd.: 412; Found: [M + H]$^+$ 413 | Method 28 |
| 16 | (R)-2-(6-Chloro-5-(5-methyl-1H-pyrazol-3-ylamino)-3H-imidazo[4,5-b]pyridin-3-yl)-2-(4-fluorophenyl)ethanol | (400 MHz) 11.95 (s, 1H), 8.46 (s, 1H), 8.10 (s, 1H), 8.02 (br s, 1H), 7.40 (m, 2H), 7.17 (m, 2H), 6.28 (s, 1H), 5.69 (br s, 1H), 5.32 (t, J = 4.8 Hz, 1H), 4.34 (m, 1H), 4.10 (m, 1H), 2.26 (s, 3H). MS: Calcd.: 386; Found: [M + H]$^+$ 387 | Method 29 |
| 17 | (R)-2-(6-Chloro-5-(5-tert-butyl-1H-pyrazol-3-ylamino)-3H-imidazo[4,5-b]pyridin-3-yl)-2-(4-fluorophenyl)ethanol | (400 MHz) 12.00 (s, 1H), 8.45 (s, 1H), 8.11 (s, 1H), 8.04 (s, 1H), 7.39 (m, 2H), 7.13 (m, 2H), 6.42 (s, 1H), 5.70 (m, 1H), 5.27 (t, J = 4.8 Hz, 1H), 4.41 (m, 1H), 4.08 (m, 1H), 1.28 (s, 9H). MS: Calcd.: 428; Found: [M + H]$^+$ 429 | Method 30 |
| 18 | 3-(4-Fluorobenzyl)-6-chloro-N-(5-cyclopropyl-1H-pyrazol-3-yl)-3H-imidazo[4,5-b]pyridin-5-amine | (400 MHz) 12.02 (s, 1H), 8.33 (s, 1H), 8.11 (s, 1H), 8.05 (s, 1H), 7.38 (m, 2H), 7.17 (m, 2H), 6.28 (s, 1H), 5.40 (s, 2H), 1.88 (m, 1H), 0.94 (m, 2H), 0.64 (m, 2H). MS: Calcd.: 382; Found: [M + H]$^+$ 383 | Method 31 |

Example 19

(S)-5-(5-Cyclopropyl-1H-pyrazol-3-ylamino)-6-fluoro-3-(1-(4-fluorophenyl)ethyl)-1H-imidazo[4,5-b]pyridin-2(3H)-one A mixture of (S)-6-(5-cyclopropyl-1H-pyrazol-3-ylamino)-5-fluoro-2-(1-(4-fluorophenyl)ethylamino)nicotinic acid (Method 40; 0.03 g, 0.08 mmol), triethylamine (0.02 g, 0.22 mmol), and DPPA (0.04 g, 0.15 mmol) in t-BuOH (2 ml) was heated to 83° C. for 5 hours. The reaction was cooled, concentrated, and then dissolved in DCM (30 ml). The organic layer was washed with water (50×2 ml), dried, filtered, and concentrated. The resulting solid was purified by column chromatography (DCM:MeOH=15:1) to give the title compounds (0.01 g, 30%). NMR (400 MHz, CD$_3$OD) 7.48-7.44 (m, 2H), 7.24 (d, J=10.3 Hz, 1H), 7.06-7.02 (m, 2H), 5.93 (br s, 1H), 5.76-5.71 (m, 1H), 1.99 (d, J=7.2 Hz, 3H), 1.90-1.84 (m, 1H), 0.96-0.94 (m, 2H), 0.64-0.63 (m, 2H). MS: Calcd.: 396. Found: [M+H]$^+$ 397.

Example 20

(S)—N-(5-Cyclopropyl-1H-pyrazol-3-yl)-3-(1-(4-fluorophenyl)ethyl)-3H-[1,2,3]triazolo[4,5-b]pyridin-5-amine To a solution of (S)—N$^6$-(5-cyclopropyl-1H-pyrazol-3-yl)-N$^2$-(1-(4-fluorophenyl)ethyl)pyridine-2,3,6-triamine (Method 9; 0.08 g, 0.2 mmol), in aqueous acetic acid (5%, 3 ml) was slowly added the aqueous NaNO$_2$ (0.01 g, 0.2 mmol, 1 ml H$_2$O) solution at 25° C. The reaction was allowed to stir for an additional 5 minutes, then quenched with water (10 ml), and extracted with DCM (3×25 ml). The combined organic was washed with saturated NaHCO$_3$ (50 ml), dried, filtered, and concentrated. The resulting solid was purified by column chromatography (DCM:MeOH=40:1) to give the title compound (0.037 g, 50%). NMR (400 MHz, CD$_3$OD) 8.02 (d, J=8.9 Hz, 1H), 7.46-7.42 (m, 2H), 7.08-7.04 (m, 2H), 6.91 (d, J=8.9 Hz, 1H), 6.23-6.19 (m, 2H), 2.12 (d, J=7.0 Hz, 3H), 1.95-1.91 (m, 1H), 1.02-1.00 (m, 2H), 0.75-0.72 (m, 2H). MS: Calcd.: 363. Found: [M+H]$^+$ 364.

Example 21

(S)—N-(5-Cyclopropyl-1H-pyrazol-3-yl)-6-fluoro-3-(1-(4-fluorophenyl)ethyl)-3H-benzo[d]imidazol-5-amine A mixture of (S)-6-bromo-5-fluoro-1-(1-(4-fluorophenyl)ethyl)-1H-benzo[d]imidazole (Method 44; 0.200 g, 0.59 mmol), 5-amino-3-cyclopropyl-1H-pyrazole-1-carboxylic acid tert-butyl ester (0.166 g, 0.741 mmol), Pd$_2$dba$_3$ (0.011 g, 0.012 mmol), Xantphos (0.021 g, 0.036 mmol), and Cs$_2$CO$_3$ (0.483 g, 1.48 mmol) in toluene (5 ml) was heated at reflux for 18 hrs. To this was added 10 ml of EtOAc and saturated NH$_4$Cl solution (10 ml). The organic layer was separated, washed with brine (10 ml), dried over Na$_2$SO$_4$, and concentrated under reduced pressure. The resulted residue was dissolved in the mixture of DCM:TFA (3:1 v/v, 4 ml), stirred at 25° C. for 2 hrs, concentrated, and treated carefully with saturated NaHCO$_3$ solution (5 ml). The aqueous layer was extracted with DCM (10 ml), dried over Na$_2$SO$_4$, concentrated under reduced pressure, and purified by column chromatography (EtOAc) to give the title compound as a white solid (0.135 g, 60%). NMR (400 MHz) 11.71 (br, 1H), 8.30 (s, 1H), 8.04 (rb, 1H), 7.91 (s, 1H), 7.40 (d, J=12 Hz, 1H), 7.31 (m, 2H), 7.18 (m, 2H), 5.67 (m, 1H), 5.53 (s, 1H), 1.93 (br, 3H), 1.84 (m, 1H), 0.92 (m, 2H), 0.65 (m, 2H). MS: Calcd.: 379; Found: [M+H]$^+$ 380.

Examples 22-23

Following a similar procedure to Example 21, the following compounds were synthesized from a suitable benzimidazole and an aminopyrazole.

| Ex | Compound | NMR/MS | SM |
|---|---|---|---|
| 22 | (S)-6-Fluoro-3-(1-(4-fluorophenyl)ethyl)-N-(5-methyl-1H-pyrazol-3-yl)-3H-benzo[d]imidazol-5-amine | (400 MHz) 11.67 (s, 1H), 8.30 (s, 1H), 8.08 (d, J = 7.6 Hz, 1H), 7.93 (s, 1H), 7.39 (d, J = 12.0 Hz, 1H), 7.32 (m, 2H), 7.18 (m, 2H), 5.67 (q, J = 7.2 Hz, 1H), 5.61 (s, 1H), 2.17 (s, 3H), 1.92 (d, J = 6.8 Hz, 3H). MS: Calcd.: 353; Found: [M + H]$^+$ 354 | Method 44 |
| 23 | (S)—N-(5-tert-Butyl-1H-pyrazol-3-yl)-6-fluoro-3-(1-(4-fluorophenyl)ethyl)-3H-benzo[d]imidazol-5-amine | (400 MHz) 11.72 (s, 1H), 8.30 (s, 1H), 8.11 (br, 1H), 7.92 (s, 1H), 7.40 (d, J = 12 Hz, 1H), 7.31 (m, 2H), 7.17 (m, 2H), 5.69 (q, J = 6.8 Hz, 1H), 5.65 (s, 1H), 1.93 (d, J = 7.2 Hz, 3H), 1.18 (s, 9H). MS: Calcd.: 395; Found: [M + H]$^+$ 396 | Method 44 |

Example 24

(S)-6-Fluoro-3-(1'-(4-fluorophenyl)ethyl)-N-(5-methyl-1H-pyrazol-3-yl)-3H-imidazo[4,5-b]pyridin-5-amine To a solution of (S)-3-fluoro-N$^6$-(1'-(4-fluorophenyl)ethyl)-N$^2$-(5-methyl-1H-pyrazol-3-yl)-5-nitropyridine-2,6-diamine (Method 47, 0.6 g, 1.6 mmol) in a mixture of MeOH-THF (1:1, 40 ml) under nitrogen was added zinc dust (0.52 g, 8.0 mmol). A saturated aqueous solution of NH$_4$Cl (4.0 ml) was then added slowly from an addition funnel over 20 minutes. Upon completion of the addition, the reaction was allowed to stir for an additional 30 minutes, at which point a saturated aqueous solution of NH$_4$OAc (5.0 ml) was added, and the reaction was stirred for 30 minutes. EtOAc (15 ml) was then added, and the reaction was stirred vigorously. The remaining solids were then filtered through celite, and the organic fraction was separated from the remaining filtrate, dried over Na$_2$SO$_4$, filtered and concentrated to give to give crude (S)-5-fluoro-N$^2$-(1'-(4-fluorophenyl)ethyl)-N$^6$-(5-methyl-1H-pyrazol-3-yl)pyridine-2,3,6-triamine (0.50 g, 90%) which was used without further purification. The above amine was immediately placed in EtOH (30 ml) and formamidine acetate (0.36 g, 3.4 mmol) was added. The reaction was flushed with nitrogen and heated to 95° C. for 12 hours. The reaction was cooled to room temperature, and a saturated aqueous NaHCO$_3$ solution (5 ml) was added, along with EtOAc (15 ml). The resulting mixture was stirred vigorously for 10 minutes. The layers were then allowed to separate, and the organic fraction was isolated, washed with brine (15 ml), dried over Na$_2$SO$_4$, filtered and concentrated. The resulting dark residue was purified by column chromatography (hexanes-EtOAc=1:30) to give the title compound (0.30 g, 48%). $^1$H NMR (400 MHz, CD$_3$OD) δ 8.29 (s, 1H), 7.57 (d, J=11.1 Hz, 1H), 7.46-7.42 (m, 2H), 7.04-7.00 (m, 2H), 6.29 (s, 1H), 5.15-5.10 (m, 1H), 2.37 (s, 3H), 1.58 (d, J=7.0 Hz, 3H). MS: Calcd.: 354. Found: [M+H]$^+$ 355.

Examples 25-29

Following a similar procedure to Example 24, the following compounds were synthesized from a suitable nitropyridine.

| Ex | Compound | NMR/MS | SM |
|---|---|---|---|
| 25 | N-(5-Cyclopropyl-1H-pyrazol-3-yl)-6-fluoro-3-(4-fluorobenzyl)-3H-imidazo[4,5-b]pyridin-5-amine | (400 MHz, CD$_3$OD) δ 8.31 (s, 1H), 7.56 (d, J = 11.2 Hz, 1H), 7.40-7.37 (m, 2H), 7.03-6.98 (m, 2H), 6.29 (s, 1H), 4.61 (s, 2H), 1.98-1.90 (m, 1H), 1.05-1.01 (m, 2H), 0.71-0.67 (m, 2H). MS: Calcd.: 366; Found: [M + H]$^+$ 367. | Method 48 |
| 26 | (R)-2-(5-(5-Cyclopropyl-1H-pyrazol-3-ylamino)-6-fluoro-3H-imidazo[4,5-b]pyridin-3-yl)-2-(4-fluorophenyl)ethanol | (400 MHz, CD$_3$OD) δ 8.32 (s, 1H), 7.60 (d, J = 10.9 Hz, 1H), 7.48-7.44 (m, 2H), 7.07-7.03 (m, 2H), 6.18 (s, 1H), 5.12-5.09 (m, 1H), 3.92-3.81 (m, 2H), 1.99-1.95 (m, 1H), 1.12-1.08 (m, 2H), 0.83-0.73 (m, 2H). MS: Calcd.: 396; Found: [M + H]$^+$ 397. | Method 49 |
| 27 | (S)—N-(5-Cyclopropyl-1H-pyrazol-3-yl)-6-fluoro-3-(1-(4-fluorophenyl)ethyl)-3H-imidazo[4,5-b]pyridin-5-amine | (400 MHz, CD$_3$OD) δ 8.25 (s, 1H), 7.49 (d, J = 11.1 Hz, 1H), 7.37-7.33 (m, 2H), 6.97-6.93 (m, 2H), 6.14 (s, 1H), 5.05-5.02 (m, 1H), 1.94-1.90 (m, 1H), 1.50 (d, J = 7.0 Hz, 3H), 1.05-1.01 (m, 2H), 0.77-0.67 (m, 2H). MS: Calcd.: 380; Found: [M + H]$^+$ 381. | Method 50 |
| 28 | (S)-6-Fluoro-3-(1-(4-fluorophenyl)ethyl)-N-(5-isopropoxy-1H-pyrazol-3-yl)-3H-imidazo[4,5-b]pyridin-5-amine | (400 MHz, CD$_3$OD) δ 8.31 (s, 1H), 7.57 (d, J = 11.1 Hz, 1H), 7.43-7.40 (m, 2H), 7.01-6.97 (m, 2H), 5.94 (s, 1H), 5.19-5.14 (m, 1H), 4.49-4.43 (s, 1H), 1.58 (d, J = 7.0 Hz, 3H), 1.45-1.37 (m, 6H). MS: Calcd.: 398; Found: [M + H]$^+$ 399. | Method 51 |
| 29 | (R)-2-(6-Fluoro-5-(5-methyl-1H-pyrazol-3-ylamino)-3H-imidazo[4,5-b]pyridin-3-yl)-2-(4-fluorophenyl)ethanol | (400 MHz, CD$_3$OD) δ 8.32 (s, 1H), 7.61 (d, J = 11.0 Hz, 1H), 7.49-7.45 (m, 2H), 7.08-7.04 (m, 2H), 6.23 (s, 1H), 5.10-5.07 (m, 1H), 3.91-3.79 (m, 2H), 2.36 (s, 3H). MS: Calcd.: 370; Found: [M + H]$^+$ 371. | Method 52 |

Example 30

(S)-6-Chloro-3-(1-(4-fluorophenyl)ethyl)-N-(5-isopropoxy-1H-pyrazol-3-yl)-3H-imidazo[4,5-b]pyridin-5-amine (S)-5-Chloro-$N^2$-(1-(4-fluorophenyl)ethyl)pyridine-$N^6$-(5-isopropoxy-1H-pyrazol-3-yl)-2,3,6-triamine (Method 57, 0.31 g, 0.77 mmol) and formamidine acetate (0.16 g, 1.5 mmol) in EtOH (5 ml) was heated at reflux overnight. Saturated sodium bicarbonate solution (10 ml) and EtOAc (30 ml) was added. The organic layer was separated, washed with brine (10 ml), and dried over sodium sulfate. The solvent was removed under reduced pressure and the residue was purified by chromatography (EtOAc-MeOH=40:1) to give the title compound as an off-white solid (0.065 g, 20%). $^1$H NMR (400 MHz) δ 11.03 (s, 1H), 9.03 (s, 1H), 8.48 (s, 1H), 8.19 (s, 1H), 7.37 (m, 2H), 7.14 (m, 2H), 6.03 (m, 1H), 5.73 (s, 1H), 4.66 (m, 1H), 1.94 (d, J=6.8 Hz, 3H), 1.28 (m, 6H). MS: Calcd.: 414. Found: [M+H]$^+$ 415.

Example 31

(S)-3-(1-(4-Fluorophenyl)ethyl)-N-(5-isopropoxy-1H-pyrazol-3-yl)-3H-imidazo[415-b]pyridin-5-amine (S)—$N^2$-(1-(4-Fluorophenyl)ethyl)pyridine-$N^6$-(5-isopropoxy-1H-pyrazol-3-yl)-2,3,6-triamine (Method 60, 0.27 g, 0.73 mmol) and formamidine acetate (0.15 g, 1.5 mmol) in EtOH (5 ml) was heated at reflux overnight. Saturated sodium bicarbonate solution (10 ml) and EtOAc (30 ml) was added. The organic layer was separated, washed with brine (10 ml), and dried over sodium sulfate. The solvent was removed under reduced pressure and the residue was purified by chromatography (EtOAc-MeOH=40:1) to give the title compound as an off-white solid (0.058 g, 21%). $^1$H NMR (400 MHz) δ 11.21 (s, 1H), 9.75 (br s, 1H), 8.37 (s, 1H), 7.86 (d, J=8.0 Hz, 1H), 7.39 (m, 2H), 7.16 (m, 2H), 6.70 (br s, 1H), 6.17 (br s, 1H), 5.34 (m, 1H), 4.67 (m, 1H), 1.93 (d, J=7.2 Hz, 3H), 1.28 (m, 6H). MS: Calcd.: 371; Found: [M+H]$^+$ 381.

Example 32

(R)-2-(4-Fluorophenyl)-2-(5-(5-methyl-1H-pyrazol-3-ylamino)-3H-imidazo[4,5-b]pyridin-3-yl)ethanol (R)-2-(3-Amino-6-(5-methyl-1H-pyrazol-3-ylamino)pyridin-2-ylamino)-2-(4-fluorophenyl)ethanol (Method 62, 0.28 g, 0.82 mmol) and formamidine acetate (0.17 g, 1.6 mmol) in EtOH (5 ml) was heated at reflux overnight. Saturated sodium bicarbonate solution (10 ml) and EtOAc (30 ml) was added. The organic layer was separated, washed with brine (10 ml) and dried over sodium sulfate. The solvent was removed under reduced pressure and the residue was purified by chromatography (EtOAc-MeOH=40:1) to give the title compound as off white solid (0.021 g, 73%). $^1$H NMR (400 MHz) δ 11.72 (s, 1H), 9.24 (s, 1H), 8.33 (s, 1H), 7.77 (d, J=8.4 Hz, 1H), 7.40 (m, 2H), 7.17 (m, 2H), 6.93 (d, J=8.0 Hz, 1H), 6.27 (s, 1H), 5.71 (br s, 1H), 5.32 (t, J=4.2 Hz, 1H), 4.34 (m, 1H), 4.12 (m, 1H), 4.03 (m, 1H), 2.22 (s, 3H). MS: Calcd.: 352. Found: [M+H]$^+$ 353.

Preparation of Starting Materials

Method 1

(2R)-2-({2-[(5-Cyclopronyl-1H-pyrazol-3-yl)amino]-5-nitropyrimidin-4-yl}amino)-2-(4-fluorophenyl)ethanol To a solution of (2R)-2-[(2-chloro-5-nitropyrimidin-4-yl)amino]-2-(4-fluorophenyl)ethanol (Method 6; 300 mg, 0.96 mmol) in EtOH (4 ml) was added a solution of 5-cyclopropyl-1H-pyrazol-3-amine (118 mg, 0.96 mmol) in EtOH (2 ml) and triethylamine (0.2 ml, 1.44 mmol). The reaction mixture was stirred at 45° C. for 18 hours. Solvent was removed and the residue was dissolved in EtOAc and was washed with water. The organic layer was concentrated. Flash chromatography on silica gel (EtOAc) gave the desired product as a yellowish solid (196 mg, 51%). NMR 0.64 (m, 2H), 0.92 (m, 2H), 1.83 (m, 1H), 3.82 (m, 2H), 5.27 (m, 2H), 5.93 (m, 1H), 7.12 (m, 2H), 7.39 (m, 2H), 8.95 (s, 1H), 9.19 (s, 1H), 10.54 (brs, 1H), 12.11 (brs, 1H).

Methods 2-5

Following a similar procedure to Method 1, the following compounds were synthesized from a nitrochloropyrimidine by reacting it with an amine.

| Method | Compound | NMR | SM | Amine |
|---|---|---|---|---|
| 2 | $N^2$-(5-Cyclopropyl-1H-pyrazol-3-yl)-$N^4$-(4-fluorobenzyl)-5-nitropyrimidine-2,4-diamine | 0.43 (m, 2H), 0.85 (m, 2H), 1.76 (m, 1H), 4.75 (m, 2H), 5.94 (m, 1H), 7.13 (m, 2H), 7.33 (m, 2H), 8.94 (s, 1H), 9.35 (s, 1H), 10.51 (br s, 1H), 12.13 (br s, 1H) | Method 7 | 5-cyclopropyl-1H-pyrazol-3-amine |
| 3 | (2R)-2-(4-Fluorophenyl)-2-({2-[(5-methyl-1H-pyrazol-3-yl)amino]-5-nitropyrimidin-4-yl}amino)ethanol | 2.18 (s, 3H), 3.80 (m, 2H), 5.26 (m, 2H), 5.90 (m, 1H), 7.15 (m, 2H), 7.43 (m, 2H), 8.95 (s, 1H), 9.20 (s, 1H), 10.5 (br s, 1H), 12.06 (br s, 1H) | Method 6 | 5-methyl-1H-pyrazol-3-amine |
| 4 | $N^2$-(5-Cyclopropyl-1H-pyrazol-3-yl)-$N^4$-[(1S)-1-(4-fluorophenyl)ethyl]-5-nitropyrimidine-2,4-diamine | (CDCl$_3$): 0.74 (m, 2H), 1.00 (m, 2H), 1.64 (m, 3H), 1.88 (m, 1H), 5.41 (m, 1H), 6.12 (m, 1H), 7.02 (m, 2H), 7.33 (m, 2H), 8.85 (s, 1H), 9.14 (s, 1H) | Method 8 | 5-cyclopropyl-1H-pyrazol-3-amine |

-continued

| Method | Compound | NMR | SM | Amine |
|---|---|---|---|---|
| 5 | $N^4$-[(1S)-1-(4-Fluorophenyl)ethyl]-$N^2$-(5-isopropoxy-1H-pyrazol-3-yl)-5-nitropyrimidine-2,4-diamine | (CDCl$_3$): 1.25 (m, 6H), 1.70 (m, 3H), 4.60 (m, 1H), 5.40 (m, 1H), 5.60 (m, 1H), 7.02 (m, 2H), 7.33 (m, 2H), 8.80 (s, 1H), 9.14 (s, 1H) | Method 8 | 5-isopropoxy-1H-pyrazol-3-amine |

Method 6

(2R)-2-[(2-Chloro-5-nitropyrimidin-4-yl)amino]-2-(4-fluorophenyl)ethanol

To a solution of 2,4-dichloro-5-nitropyrimidine (1.5 g, 7.73 mmol) in EtOH (25 ml) at 0° C. was added triethylamine (1.6 ml, 11.6 mmol) and a solution of (2R)-2amino-2-(4-fluorophenyl)ethanol (prepared according to a procedure in *J. Med. Chem.* 1999, 42, 4981-5001, 1.2 g, 7.73 mmol). The reaction mixture was stirred at 0° C. for 3 hours. The solvent was removed and the residue was dissolved in EtOAc and was washed with water. The organic layer was concentrated. Flash chromatography on silica gel (20-50% EtOAc in hexanes) gave the title compound as a solid (703 mg, 29%). NMR (CDCl$_3$) 4.00 (m, 2H), 5.50 (m, 1H), 7.07 (m, 2H), 7.38 (m, 2H), 9.04 (s, 1H), 9.10 (br s, 1H).

Methods 7-8

Following a similar procedure to Method 6, the following compounds were synthesized from a 2,4-dichloro-5-nitropyrimidine by reacting it with an amine.

| Method | Product | NMR | Amine |
|---|---|---|---|
| 7 | 6-Chloro-N-(4-fluorobenzyl)-3-nitropyridin-2-amine | (CDCl$_3$): 4.82 (m, 2H), 7.05 (m, 2H), 7.37 (m, 2H), 8.59 (m, 1H), 9.08 (s, 1H) | (4-fluorobenzyl)amine |
| 8 | 6-Chloro-N-[(1S)-1-(4-fluorophenyl)ethyl]-3-nitropyridin-2-amine | (CDCl$_3$): 1.65 (m, 3H), 5.51 (m, 1H), 7.05 (m, 2H), 7.37 (m, 2H), 8.59 (m, 1H), 9.03 (s, 1H) | [(1S)-1-(4-fluorophenyl)ethyl]amine |

Method 9

(S)—$N^6$-(5-Cyclopropyl-1H-pyrazol-3-yl)-$N^2$-(1-(4-fluorophenyl)ethyl)pyridine-2,3,6-triamine To a suspension of (S)—$N^6$-(5-cyclopropyl-1H-pyrazol-3-yl)-$N^2$-(1-(4-fluorophenyl)ethyl)-3-nitropyridine-2,6-diamine (Method 14; 0.40 g, 1.05 mmol) and Zinc dust (0.342 g, 5.23 mmol) in MeOH:THF (1:1, 16 ml) was slowly added a saturated aqueous ammonium chloride solution (2.5 ml). The mixture was stirred at 25° C. for 1 hour, then treated with saturated ammonium acetate solution (4 ml). The resulting mixture was stirred for another 30 minutes. Zn dust was removed by filtration and the cake was washed with EtOAc (20 ml). The organic layer was separated, washed with brine (10 ml), dried over Na$_2$SO$_4$, and concentrated. The crude product was used directly for the next step without purification. MS: Calcd.: 352. Found: [M+H]$^+$ 353.

Methods 10-13

Following a similar procedure to Method 9, the following compounds were synthesized from a nitropyridine by reacting it with zinc dust.

| Method | Product | MS | SM |
|---|---|---|---|
| 10 | $N^6$-(5-Cyclopropyl-1H-pyrazol-3-yl)-$N^2$-(4-fluorobenzyl)pyridine-2,3,6-triamine | Calcd.: 338; Found: [M + H]$^+$ 339 | Method 15 |
| 11 | (2R)-2-({3-Amino-6-[(5-cyclopropyl-1H-pyrazol-3-yl)amino]pyridin-2-yl}amino)-2-(4-fluorophenyl)ethanol | Calcd.: 368; Found: [M + H]$^+$ 369 | Method 16 |
| 12 | 2-({3-Amino-6-[(5-cyclopropyl-1H-pyrazol-3-yl)amino]pyridin-2-yl}amino)-2-(4-fluorophenyl)propane-1,3-diol | Calcd.: 398; Found: [M + H]$^+$ 399 | Method 17 |

-continued

| Method | Product | MS | SM |
|---|---|---|---|
| 13 | N⁶-(5-Cyclopropyl-1H-pyrazol-3-yl)-N²-[(1R)-1-(4-fluorophenyl)ethyl]pyridine-2,3,6-triamine | Calcd.: 352; Found: [M + H]⁺ 353 | Method 18 |

Method 14

(S)—N⁶-(5-Cyclopropyl-1H-pyrazol-3-yl)-N²-(1-(4-fluoro-phenyl)ethyl)-3-nitropyridine-2,6-diamine A mixture of (S)-6-chloro-N-(1-(4-fluorophenyl)ethyl)-3-nitropyridin-2-amine (Method 19; 1.74 g, 5.88 mmol), 5-cyclopropyl-1H-pyrazol-3-amine (0.91 g, 7.36 mmol), and DIEA (1.28 ml, 7.36 mmol) in n-BuOH (10 ml) was heated in a sealed tube at 160° C. for 60 hours. The solvent was removed under reduced pressure and the residue was purified by chromatography (hexane: EtOAc=1:1) to give the title compound as a yellow solid (1.35 g, 60%). NMR (400 MHz) 12.15 (s, 1H), 10.43 (br, 1H), 9.19 (br, 1H), 8.12 (d, J=9.2 Hz, 1H), 7.45 (m, 2H), 7.17 (m, 2H), 6.25 (br, 1H), 6.14 (br, 1H), 5.45 (m, 1H), 1.87 (m, 1H), 1.60 (d, J=6.8 Hz, 3H), 0.95 (m, 2H), 0.65 (m, 2H). MS: Calcd.: 382. Found: [M+H]⁺ 383.

Methods 15-18

Following a similar procedure to Method 14, the following compounds were synthesized from a chloronitropyridine by reacting it with an amine.

Method 19

(S)-6-Chloro-N-(1-(4-fluorophenyl)ethyl)-3-nitropyridin-2-amine

To a mixture of 2,6-dichloro-3-nitropyridine (2.26 g, 10.8 mmol) and potassium carbonate (1.29 g, 9.34 mmol) in anhydrous CH₃CN (20 ml), was added (S)-1-(4-fluoro-phenyl)-ethylamine (1.00 g, 7.19 mmol) dropwise at 0° C. The reaction mixture was stirred at 25° C. for 17 hours. The solid was removed by filtration and the resulted cake was washed with EtOAc (20 ml). The combined filtrate was concentrated and purified by column chromatography (hexane:EtOAc=10:1) to give the title compound as a yellow solid (1.74 g, 82%). NMR (400 MHz) 8.65 (d, J=7.6 Hz, 1H), 8.43 (d, J=8.4 Hz, 1H), 7.51 (m, 2H), 7.16 (m, 2H), 6.81 (d, J=8.8 Hz, 1H), 5.37 (m, 1H), 1.59 (d, J=6.8 Hz, 3H).

Methods 20-23

Following a similar procedure to Method 19, the following compounds were synthesized from a 2,6-dichloro-3-nitropyridine by reacting it with an amine.

| Method | Product | NMR/MS | Amine | SM |
|---|---|---|---|---|
| 15 | N⁶-(5-Cyclopropyl-1H-pyrazol-3-yl)-N²-(4-fluorobenzyl)-3-nitropyridine-2,6-diamine | (400 MHz,) 12.10 (br s, 1H), 10.40 (br s, 1H), 9.43 (br, 1H), 8.09 (d, J = 6.8 Hz, 1H), 7.37 (m, 2H), 7.15 (m, 2H), 6.24 (br s, 1H), 6.04 (br s, 1H), 4.80 (d, J = 5.6 Hz, 2H), 1.772 (m, 1H), 0.85 (m, 2H), 0.46 (m, 2H). MS: Calcd.: 368; Found: [M + H]⁺ 369 | 5-cyclopropyl-1H-pyrazol-3-amine | Method 20 |
| 16 | (2R)-2-({6-[(5-Cyclopropyl-1H-pyrazol-3-yl)amino]-3-nitropyridin-2-yl}amino)-2-(4-fluorophenyl)ethanol | (400 MHz) 12.10 (s, 1H), 10.39 (br s, 1H), 9.57 (br s, 1H), 8.11 (d, J = 9.2 Hz, 1H), 7.28 (m, 2H), 7.15 (m, 2H), 6.23 (br s, 1H), 5.76 (s, 1H), 5.35 (br s, 1H), 5.19 (t, J = 4.8 Hz, 1H), 3.86 (m, 1H), 3.75 (m, 1H), 1.87 (m, 1H), 0.95 (m, 2H), 0.64 (m, 2H). MS: Calcd.: 398; Found: [M + H]⁺ 399 | 5-cyclopropyl-1H-pyrazol-3-amine | Method 21 |
| 17 | 2-({6-[(5-Cyclopropyl-1H-pyrazol-3-yl)amino]-3-nitropyridin-2-yl}amino)-2-(4-fluorophenyl)propane-1,3-diol | (400 MHz) 11.94 (s, 1H), 10.15 (br s, 1H), 9.85 (s, 1H), 8.12 (d, J = 9.2 Hz, 1H), 7.40 (m, 2H), 7.13 (m, 2H), 6.19 (br s, 1H), 2.86 (br s, 2H), 4.44 (m, 4H), 1.65 (m, 1H), 0.87 (m, 2H), 0.47 (m, 2H). MS: Calcd.: 428; Found: [M + H]⁺ 429. | 5-cyclopropyl-1H-pyrazol-3-amine | Method 22 |
| 18 | N⁶-(5-Cyclopropyl-1H-pyrazol-3-yl)-N²-[(1R)-1-(4-fluorophenyl)ethyl]-3-nitropyridine-2,6-diamine | MS: Calcd.: 382; Found: [M + H]⁺ 383. | 5-cyclopropyl-1H-pyrazol-3-amine | Method 23 |

| Method | Product | NMR/MS | Amine |
|---|---|---|---|
| 20 | 6-Chloro-N-(4-fluorobenzyl)-3-nitropyridin-2-amine | (400 MHz, CDCl₃) 8.58 (br s, 1H), 8.37 (d, J = 8.4 Hz, 1H), 7.36 (m, 2H), 7.04 (m, 2H), 6.67 (d, J = 8.4 Hz, 1H), 4.78 (d, J = 5.6 Hz, 2H) | (4-fluoro-phenyl)methanamine |
| 21 | (2R)-2-[(6-Chloro-3-nitropyridin-2-yl)amino]-2-(4-fluorophenyl)ethanol | (400 MHz) 8.96 (d, J = 7.6 Hz, 1H), 8.46 (d, J = 8.4 Hz, 1H), 7.45 (m, 2H), 7.15 (m, 2H), 6.81 (d, J = 8.8 Hz, 1H), 5.27 (m, 2H), 3.80 (m, 2H) | (R)-2-amino-2-(4-fluorophenyl)ethanol |
| 22 | 2-[(6-Chloro-3-nitropyridin-2-yl)amino]-2-(4-fluorophenyl)propane-1,3-diol | (400 MHz) 9.13 (s, 1H), 8.44 (d, J = 8.4 Hz, 1H), 7.39 (m, 2H), 7.06 (m, 2H), 6.73 (d, J = 8.8 Hz, 1H), 5.16 (t, J = 5.6 Hz, 2H), 4.07 (m 2H), 3.96 (m, 2H). MS: Calcd.: 341; Found: [M + H]⁺ 342 | Method 24 |
| 23 | 6-Chloro-N-[(1R)-1-(4-fluorophenyl)ethyl]-3-nitropyridin-2-amine | MS: Calcd.: 295; Found: [M + H]⁺ 296 | (R)-1-(4-fluorophenyl)ethanamine |

Method 24

2-Amino-2-(4-fluorophenyl)propane-1,3-diol

A suspension of 2-(4-fluorophenyl)-2-nitroproane-1,3-diol (Method 25; 4.5 g, 20.9 mmol) and Raney nickel (0.45 g, 5.23 mmol) in MeOH (50 ml) was degassed and stirred under H₂ (48 psi) for 2 hours. The catalyst was removed by filtration. The filtrate was concentrated and recrystallized from hexane:EtOAc (1:1) to give the title compound (2.35 g, 61%) as a white solid. NMR (400 MHz) 7.55 (m, 2H), 7.07 (m, 2H), 4.65 (t, J=5.2 Hz, 2H), 3.49 (m, 4H), 1.76 (s, 2H).

Method 25

2-(4-Fluorophenyl)-2-nitroproane-1,3-diol

To a solution of 1-fluoro-4-(nitromethyl)benzene (Method 26; 10.0 g, 80% pure; 52 mmol) and TEA (15.1 ml, 108.3 mmol) in dioxane (50 ml) was added formaldehyde (8.6 ml, 116 mmol) dropwise at 0° C. After addition, the reaction was slowly warmed up to 25° C. overnight. The solvent was removed under reduced pressure and the residue was purified by column chromatography (hexane:EtOAc=10:1) to give the title compound as a white solid (4.5 g, 41%). NMR (400 MHz) 7.41 (m, 2H), 7.22 (m, 2H), 5.39 (t, J=5.2 Hz, 2H), 4.22 (m, 4H).

Method 26

1-Fluoro-4-(nitromethyl)benzene

A mixture of 1-(bromomethyl)-4-fluorobenzene (11.52 g, 61 mmol) and AgNO₂ (11.3 g, 73 mmol) in benzene (200 ml) was stirred vigorously at 25° C. for 25 hrs. The solid was removed by filtration and washed with diethyl ether (500 ml). The combined organic was concentrated to give the title compound (10.0 g, 80% pure; 85%) which was used without further purification. NMR (400 MHz, CDCl₃) 7.44 (m, 2H), 7.18 (m, 2H), 5.42 (s, 2H).

Method 27

(S)-5-Chloro-N⁶-(5-cyclopropyl-1H-pyrazol-3-yl)-N²-(1-(4-fluorophenyl)ethyl)pyridine-2,3,6-triamine To a suspension of (S)-3-chloro-N²-(5-cyclopropyl-1H-pyrazol-3-yl)-N-(1-(4-fluorophenyl)ethyl)-5-nitropyridin-2,6-diamine (Method 32; 0.57 g, 1.37 mmol) and zinc dust (0.447 g, 6.84 mmol) in MeOH:THF (1:1, 24 ml) was slowly added saturated ammonium chloride solution (3.5 ml). The reaction mixture was stirred at 25° C. for 2 hours, followed by addition of saturated ammonium acetate solution (5 ml). The resulting mixture was stirred for another 30 minutes. Zn dust was removed by filtration and washed with EtOAc (20 ml). The organic layer was separated, washed with brine (10 ml), and dried over Na₂SO₄. After removal of solvent, the crude product was used directly for the next step without further purification. MS: Calcd.: 386. Found: [M+H]⁺ 387.

Methods 28-31

Following a similar procedure to Method 27, the following compounds were synthesized from a nitropyridine by reacting it with zinc dust.

| Method | Product | NMR/MS | SM |
|---|---|---|---|
| 28 | (2R)-2-({3-Amino-5-chloro-6-[(5-cyclopropyl-1H-pyrazol-3-yl)amino]pyridin-2-yl}amino)-2-(4-fluorophenyl)ethanol | MS: Calcd.: 402; Found: [M + H]⁺ 403 | Method 33 |
| 29 | (2R)-2-({3-Amino-5-chloro-6-[(5-methyl-1H-pyrazol-3-yl)amino]pyridin-2-yl}amino)-2-(4-fluorophenyl)ethanol | MS: Calcd.: 376; Found: [M + H]⁺ 377 | Method 34 |

-continued

| Method | Product | NMR/MS | SM |
|---|---|---|---|
| 30 | (2R)-2-({3-Amino-6-[(5-tert-butyl-1H-pyrazol-3-yl)amino]-5-chloropyridin-2-yl}amino)-2-(4-fluorophenyl)ethanol | MS: Calcd.: 418; Found: [M + H]+ 419 | Method 35 |
| 31 | 5-Chloro-N6-(5-cyclopropyl-1H-pyrazol-3-yl)-N2-(4-fluorobenzyl)pyridine-2,3,6-triamine | MS: Calcd.: 372; Found: [M + H]+ 373 | Method 36 |

Method 32

(S)-3-Chloro-$N^2$-(5-cyclopropyl-1H-pyrazol-3-yl)-$N^6$-(1-(4-fluorophenyl)ethyl)-5-nitropyridin-2,6-diamine A mixture of (S)-5,6-chloro-N-(1-(4-fluorophenyl)ethyl)-3-nitropyridin-2-amine (Method 37; 0.61 g, 79% pure, 1.46 mmol), 5-cyclopropyl-1H-pyrazol-3-amine (0.27 g, 2.19 mmol), and DIEA (0.38 ml, 2.19 mmol) in n-BuOH (5 ml) was heated in a sealed tube at 100° C. for 48 hours. The solvent was removed under reduced pressure and the residue was purified by column chromatography (hexane:EtOAc=2:1) to give the title compound as a yellow solid (0.57 g, 94%). NMR (400 MHz) 12.34 (s, 1H), 9.34 (s, 1H), 8.93 (d, J=7.6 Hz, 1H), 8.26 (s, 1H), 7.32 (m, 2H), 7.12 (m, 2H), 6.01 (s, 1H), 5.29 (m, 1H), 1.91 (m, 1H), 1.56 (d, J=7.2 Hz, 3H), 0.96 (m, 2H), 0.65 (m, 2H). MS: Calcd.: 416. Found: [M+H]+ 417.

Methods 33-36

Following a similar procedure to Method 32, the following compounds were synthesized from a chloronitropyridine by reacting it with an amine.

Method 37

(S)-5,6-Chloro-N-(1-(4-fluorophenyl)ethyl)-3-nitropyridin-2-amine

To a mixture of 2,3,6-trichloro-5-nitropyridine (1.00 g, 4.40 mmol) and potassium carbonate (0.79 g, 5.7 mmol) in anhydrous acetonitrile (10 ml) was added (S)-1-(4-fluorophenyl)-ethylamine (0.64 g, 4.62 mmol) dropwise at 0° C. After addition, the reaction mixture was stirred at 25° C. for 17 hours. The solid was removed by filtration and washed with EtOAc (20 ml). After evaporation of the solvent, the resulted residue was purified by column chromatography (hexane:EtOAc=10:1) to give the title compound as a yellow solid (0.61 g, 79% pure, 33%). NMR (400 MHz, CDCl$_3$) 8.46 (br s, 2H), 7.36 (m, 2H), 7.03 (m, 2H), 5.40 (m, 1H), 1.63 (d, J=6.8 Hz, 3H).

Methods 38-39

Following a similar procedure to Method 37, the following compounds were synthesized from a 2,3,6-trichloro-5-nitropyridine by reacting it with an amine.

| Method | Product | NMR/MS | Amine | SM |
|---|---|---|---|---|
| 33 | (2R)-2-({5-Chloro-6-[(5-cyclopropyl-1H-pyrazol-3-yl)amino]-3-nitropyridin-2-yl}amino)-2-(4-fluorophenyl)ethanol | (400 MHz) 12.28 (s, 1H), 9.33 (d, J = 7.6 Hz, 1H), 9.28 (s, 1H), 8.27 (s, 1H), 7.30 (m, 2H), 7.13 (m, 1H), 5.94 (s, 1H), 5.22 (br s, 2H), 3.84-3.73 (m, 2H), 1.90 (m, 1H), 0.97 (m, 2H), 0.68 (m, 2H). MS: Calcd.: 432; Found: [M + H]+ 433 | 5-cyclopropyl-1H-pyrazol-3-amine | Method 38 |
| 34 | (2R)-2-({5-Chloro-6-[(5-methyl-1H-pyrazol-3-yl)amino]-3-nitropyridin-2-yl}amino)-2-(4-fluorophenyl)ethanol | (400 MHz) 12.23 (s, 1H), 9.35 (d, J = 7.2 Hz, m), 9.30 (s, 1H), 8.27 (s, 1H), 7.32 (m 2H), 7.14 (m, 2H), 5.86 (s, 1H), 5.23 (t, J = 4.8 Hz, 1H), 5.18 (m, 1H), 3.81 (m, 1H), 3.74 (m, 1H), 2.23 (s, 3H). MS: Calcd.: 406; Found: [M + H]+ 407 | 5-methyl-1H-pyrazol-3-amine | Method 38 |
| 35 | (2R)-2-({6-[(5-tert-Butyl-1H-pyrazol-3-yl)amino]-5-chloro-3-nitropyridin-2-yl}amino)-2-(4-fluorophenyl)ethanol | (400 MHz) 12.36 (s, 1H), 9.30 (s, 1H), 9.29 (d, J = 7.6 Hz, 1H), 8.27 (s, 1H), 7.26 (m 2H), 7.08 (m, 2H), 6.18 (s, 1H), 5.29 (m, 1H), 5.21 (t, J = 4.8 Hz, 1H), 3.81 (m, 2H), 1.28 (s, 9H). MS: Calcd.: 448; Found: [M + H]+ 449 | 5-tert-butyl-1H-pyrazol-3-amine | Method 38 |
| 36 | 3-Chloro-$N^2$-(5-cyclopropyl-1H-pyrazol-3-yl)-$N^6$-(4-fluorobenzyl)-5-nitropyridine-2,6-diamine | (400 MHz) 12.33 (s, 1H), 9.32 (br s, 1H), 8.26 (s, 1H), 8.20 (br s, 1H), 7.53 (m, 2H), 7.11 (m, 1H), 5.96 (s, 1H), 4.69 (d, J = 6.0 Hz, 2H), 1.79 (m, 1H), 0.87 (m, 2H), 0.47 (m, 2H). sMS: Calcd.: 402; Found: [M + H]+ 403 | (4-fluorophenyl)-methanamine | Method 39 |

| Method | Product | NMR/MS | Amine |
|---|---|---|---|
| 38 | (2R)-2-[(5,6-Dichloro-3-nitropyridin-2-yl)amino]-2-(4-fluorophenyl)ethanol | (400 MHz) 8.91 (d, J = 7.2 Hz, 1H), 8.66 (s, 1H), 7.45 (m, 2H), 7.15 (m, 2H), 5.25 (m, 2H), 3.80 (m, 2H) | (R)-2-amino-2-(4-fluorophenyl)ethanol |
| 39 | 3,6-Dichloro-N-(5-cyclopropyl-1H-pyrazol-3-yl)-5-nitropyridin-2-amine | (400 MHz) 12.37 (s, 1H), 9.83 (s, 1H), 8.54 (s, 1H), 6.27 (s, 1H), 1.94 (m, 1H), 0.95 (m, 2H), 0.70 (m, 2H). MS: Calcd.: 313; Found: [M + H]$^+$ 314 | 5-cyclopropyl-1H-pyrazol-3-amine |

Method 40

(S-6-(5-Cyclopropyl-1H-pyrazol-3-ylamino)-5-fluoro-2-(1-(4-fluorophenyl)ethylamino)nicotinic acid (S)-6-(5-Cyclopropyl-1H-pyrazol-3-ylamino)-5-fluoro-2-(1-(4-fluorophenyl)ethylamino)nicotinamide (Method 41; 1.0 g, 2.5 mmol) was dissolved in a 10% aqueous EtOH solution (10 ml) at 25° C., followed by addition of solid KOH (2.8 g, 50.0 mmol). The reaction solution was heated to 95° C. for 4 days, cooled to 25° C., and extracted with DCM (2×50 ml). The aqueous layer was then acidified to pH 3. The resulting solid (0.55 g), was collected by filtration and dried under vacuum. MS: Calcd.: 399. Found: [M+H]$^+$ 400.

Method 41

(S)-6-(5-Cyclopropyl-1H-pyrazol-3-ylamino)-5-fluoro-2-(1-(4-fluorophenyl)ethylamino)nicotinamide To a solution of (S)-6-(5-cyclopropyl-1H-pyrazol-3-ylamino)-5-fluoro-2-(1-(4-fluorophenyl)ethylamino)nicotinonitrile (Method 42; 0.5 g, 1.3 mmol) in MeOH (50 ml) was added KOH solution (25%, 2 ml), followed by addition of H$_2$O$_2$ (30%, 0.1 ml). The resulting dark red solution was heated to 65° C. for 1 hour, cooled, and concentrated. The resulting residue was dissolved in EtOAc (50 ml), washed with water (30 ml), dried, filtered, and concentrated. The resulting solid was purified by column chromatography (DCM:MeOH=30:1) to give the title compound (0.30 g, 60%). MS: Calcd.: 398. Found: [M+H]$^+$ 399.

Method 42

(S)-6-(5-Cyclopropyl-1H-pyrazol-3-ylamino)-5-fluoro-2-(1-(4-fluorophenyl)ethylamino)nicotinonitrile A mixture of 2-chloro-6-(5-cyclopropyl-1H-pyrazol-3-ylamino)-5-fluoronicotinonitrile (Method 43; 0.8 g, 2.8 mmol), (S)-1-(4-fluorophenyl)ethanamine (0.8 g, 5.6 mmol), and DIEA (0.5 g, 3.7 mmol) in n-BuOH (4 ml) was heated in a sealed tube at 140° C. for 48 hrs. The reaction mixture was concentrated and purified by column chromatography (DCM:MeOH=50:1) to give the title compound (0.55 g, 50%). MS: Calcd.: 380. Found: [M+H]$^+$ 381.

Method 43

2-Chloro-6-(5-cyclopropyl-1H-pyrazol-3-ylamino)-5-fluoronicotinonitrile

A solution of 5-cyclopropyl-1H-pyrazol-3-amine (1.9 g, 16.0 mmol) in CH$_3$CN (20 ml) was added dropwise to a solution of 2,6-dichloro-5-fluoronicotinonitrile (3.0 g, 16.0 mmol) and triethylamine (2.1 g, 20.0 mmol) in CH$_3$CN (80 ml) at 25° C. The resulting solution was heated to 82° C. for 18 hrs, and then cooled to 25° C. The resulted precipitate was collected by filtration and washed with CH$_3$CN (100 ml) to give the title compound (3.2 g, 73%). MS: Calcd.: 277. Found: [M+H]$^+$ 278.

Method 44

(S)-6-Bromo-5-fluoro-1-(1-(4-fluorophenyl)ethyl)-1H-benzo[d]imidazole

A mixture of (S)-5-bromo-4-fluoro-N'-(1-(4-fluorophenyl)ethyl)benzene-1,2-diamine (Method 45; 0.62 g, 1.90 mmol) and formamidine acetate (0.316 g, 3.03 mmol) in EtOH (5 ml) was heated at reflux for 5 hours. After cooling to 25° C., the reaction mixture was treated with saturated sodium bicarbonate solution (10 ml) and EtOAc (30 ml). The organic layer was separated, washed with brine (10 ml), dried over Na$_2$SO$_4$, concentrated, and purified by column chromatography (hexane:EtOAc=1:5) to give the title compound as a white solid (0.522 g, 82%). NMR (400 MHz, CDCl$_3$) 8.06 (s, 1H), 7.56 (d, J=8.8 Hz, 1H), 7.32 (d, J=5.6 Hz, 1H), 7.15 (m, 2H), 7.06 (m, 2H), 5.54 (q, J=6.8 Hz, 1H), 1.98 (d, J=6.8 Hz, 3H). MS: Calcd.: 336. Found: [M+H]$^+$ 337.

Method 45

(S)-5-Bromo-4-fluoro-N$^1$-(1-(4-fluorophenyl)ethyl)benzene-1,2-diamine

To a suspension of (S)-5-bromo-4-fluoro-N-(1-(4-fluorophenyl)ethyl)-2-nitrobenzenamine (Method 46; 0.63 g, 1.76 mmol) and zinc dust (0.554 g, 8.47 mmol) in MeOH:THF (1:1, 24 ml) was slowly added the saturated ammonium chloride solution (4 ml). The reaction mixture was stirred at 25° C. for 2 hours followed by addition of saturated ammonium acetate solution (5 ml). The resulting mixture was stirred for another 30 minutes. Zn dust was removed by filtration and washed with EtOAc (20 ml). The organic layer was separated, washed with brine (10 ml), dried over Na$_2$SO$_4$, and concentrated under reduced pressure to give the crude product which was directly used for the next step without further purification. MS: Calcd.: 326. Found: [M+H]$^+$ 327.

Method 46

(S)-5-Bromo-4-fluoro-N-(1-(4-fluorophenyl)ethyl)-2-nitrobenzenamine

A solution of 1-bromo-2,5-difluoro-4-nitrobenzene (0.464 g, 1.95 mmol), (S)-1-(4-fluoro-phenyl)-ethylamine (0.298 g, 2.14 mmol), and DIEA (0.41 ml, 2.34 mmol) in n-BuOH (5 ml) was heated at 80° C. for 17 hours. The solvent was removed under reduced pressure and the residue was purified by column chromatography (hexane:EtOAc=5:1) to give the title compound as a yellow solid (0.63 g, 96%). NMR (400 MHz, CDCl$_3$) 8.23 (br, 1H), 7.95 (d, J=8.8 Hz, 1H), 7.29 (m, 2H), 7.08 (m, 2H), 6.84 (d, J=5.6 Hz, 1H), 4.62 (m, 1H), 1.63 (d, J=6.8 Hz, 3H).

Method 47

(S)-3-Fluoro-N$^6$-(1-(4-fluorophenyl)ethyl)-N$^2$-(5-methyl-1H-pyrazol-3-yl)-5-nitropyridine-2,6-diamine To a solution of (S)-5,6-difluoro-N-(1-(4-fluorophenyl)ethyl)-3-nitropyridin-2-amine (Method 53, 0.70 g, 2.3 mmol) in THF (12 ml) was added DIEA (0.39 g, 3.0 mmol) and 5-methyl-1H-pyrazol-3-amine (0.45 g, 4.7 mmol). The reaction was heated to 55° C. for 24 hours, cooled to room temperature, and quenched with water. The reaction was extracted with DCM (2×75 ml), and the combined organic fractions were dried over Na$_2$SO$_4$, filtered, and concentrated. The resulting oil was purified by column chromatography (DCM-MeOH=100:1) to give the title compound (0.60 g, 68%). MS: Calcd.: 374. Found: [M+H]$^+$ 375.

Method 48-52

Following a similar procedure to Method 47, the following compounds were synthesized from a nitropyridine by reacting it with a pyrazole amine.

Method 53

(S)-5,6-Difluoro-N-(1-(4-fluorophenyl)ethyl)-3-nitropyridin-2-amine

A solution of 2,3,6-trifluoro-5-nitropyridine (Method 56, 2.0 g, 11.2 mmol) in THF (50 ml) was cooled to 0° C., to which was added (S)-1-(4-fluorophenyl)ethanamine (1.56 g, 11.2 mmol). The reaction was stirred at 0° C. for 30 min., then quenched with water (50 ml) and extracted with DCM (2×75 ml). The combined organic fractions were dried over Na$_2$SO$_4$, filtered, and then concentrated. The resulting oil was purified by column chromatography (hexanes-DCM=1:1) to give the title compound (2.3 g, 70%).

Method 54-55

Following a similar procedure to Method 53, the following compounds were synthesized from 2,3,6-trifluoro-5-nitropyridine by reacting it with an amine.

| Method | Product | NMR/MS | Amine |
|---|---|---|---|
| 54 | 5,6-Difluoro-N-(4-fluorobenzyl)-3-nitropyridin-2-amine | MS: Calcd.: 283; Found: [M + H]$^+$ 284. | (4-fluorophenyl)-methanamine |

| Method | Product | NMR/MS | Amine | SM |
|---|---|---|---|---|
| 48 | N$^2$-(5-Cyclopropyl-1H-pyrazol-3-yl)-3-fluoro-N$^6$-(4-fluorobenzyl)-5-nitropyridine-2,6-diamine | MS: Calcd.: 386; Found: [M + H]$^+$ 387. | 5-cyclopropyl-1H-pyrazol-3-amine | Method 54 |
| 49 | (R)-2-(6-(5-Cyclopropyl-1H-pyrazol-3-ylamino)-5-fluoro-3-nitropyridin-2-ylamino)-2-(4-fluorophenyl)ethanol | δ 10.84 (s, 1H), 8.02 (d, J = 10.7 Hz, 1H), 7.35-7.31 (m, 2H), 7.10-7.06 (m, 2H), 6.21-6.19 (m, 1H), 5.80 (br s, 1H), 4.07 (dd, J = 11.3 and 3.9 Hz, 1H), 3.99 (dd, J = 11.3 and 6.4 Hz, 1H), 1.88-1.86 (m, 1H), 1.62 (br s, 1H), 0.98-0.95 (m, 2H), 0.70-0.68 (m, 2H). MS: Calcd.: 416; Found: [M + H]$^+$ 417. | 5-cyclopropyl-1H-pyrazol-3-amine | Method 55 |
| 50 | (S)—N$^2$-(5-Cyclopropyl-1H-pyrazol-3-yl)-3-fluoro-N$^6$-(1-(4-fluorophenyl)ethyl)-5-nitropyridine-2,6-diamine | (400 MHz, CD$_3$OD) δ 8.00 (d, J = 11.1 Hz, 1H), 7.38-7.35 (m, 2H), 7.07-7.02 (m, 2H), 6.17 (s, 1H), 5.41-5.39 (m, 1H), 1.93-1.87 (m, 1H), 1.61 (d, J = 7.0 Hz, 3H), 1.02-1.00 (m, 2H), 0.69-0.66 (m, 2H). MS: Calcd.: 400; Found: [M + H]$^+$ 401. | 5-cyclopropyl-1H-pyrazol-3-amine | Method 53 |
| 51 | (S)-3-Fluoro-N$^6$-(1-(4-fluorophenyl)ethyl)-N$^2$-(5-isopropoxy-1H-pyrazol-3-yl)-5-nitropyridine-2,6-diamine | (400 MHz, CD$_3$OD) δ 8.00 (d, J = 10.9 Hz, 1H), 7.45-7.35 (m, 2H), 7.07-7.03 (m, 2H), 5.88-5.71 (m, 1H), 5.48-5.30 (m, 1H), 4.58-4.29 (m, 1H), 1.68-1.56 (m, 3H), 1.34-1.28 (m, 6H). MS: Calcd.: 418; Found: [M + H]$^+$ 419. | 5-isopropoxy-1H-pyrazol-3-amine | Method 53 |
| 52 | (R)-2-(5-Fluoro-6-(5-methyl-1H-pyrazol-3-ylamino)-3-nitropyridin-2-ylamino)-2-(4-fluorophenyl)ethanol | δ 10.85 (br s, 1H), 8.02 (d, J = 10.5 Hz, 1H), 7.34-7.31 (m, 2H), 7.10-7.06 (m, 2H), 6.26-6.25 (m, 1H), 5.86 (br s, 1H), 5.30-5.27 (m, 1H), 4.07 (dd, J = 11.3 and 3.9 Hz, 1H), 3.97 (dd, J = 11.1 and 6.2 Hz, 1H), 2.27 (s, 3H), 1.61 (br s, 1H). MS: Calcd.: 390; Found: [M + H]$^+$ 391. | 5-methyl-1H-pyrazol-3-amine | Method 54 |

-continued

| Method | Product | NMR/MS | Amine |
|---|---|---|---|
| 55 | (R)-2-(5,6-Difluoro-3-nitropyridin-2-ylamino)-2-(4-fluorophenyl)ethanol | MS: Calcd.: 313; Found: [M + H]$^+$ 314. | (R)-2-Amino-2-(4-fluorophenyl)-ethanol |

Method 56

2,3,6-Trifluoro-5-nitropyridine

To neat 2,3,6-trifluoropyridine (12.0 g, 90 mmol) was slowly added fuming HNO$_3$ (142 g, 2254 mmol) and H$_2$SO$_4$ (133 g, 1353 mmol) slow enough to keep the internal temperature below 40° C. Upon completion of the addition, the resulting solution was heated to 60° C. for 30 minutes, and then cooled to 0° C. Ice water (2 L) was then added, and the reaction mixture was extracted with hexanes (2×300 ml) and then DCM (1×300 ml). The combined organic fractions were dried over Na$_2$SO$_4$, filtered, and concentrated to give the title compound (8.1 g, 50%), which was used without further purification.

Method 57

(S)-5-Chloro-N$^2$-(1-(4-fluorophenyl)ethyl)pyridine-N$^6$-(5-isopropoxy-1H-pyrazol-3-yl)-2,3,6-triamine A solution of saturated ammonium chloride (3 ml) was added slowly to a suspension of (S)-3-chloro-N$^6$-(1-(4-fluorophenyl)ethyl)-N$^2$-(5-isopropoxy-1H-pyrazol-3-yl)-5-nitropyridine-2,6-diamine (Method 58, 0.32 g, 0.74 mmol) and zinc dust (0.24 g, 3.7 mmol) in MeOH-THF (1:1, 20 ml). The mixture was stirred at 25° C. for 1 hour. Saturated ammonium acetate solution (5 ml) was added and the mixture was stirred for another 30 minutes. Zn dust was removed by filtration and the cake was washed with EtOAc (20 ml). The organic layer was separated, washed with brine (10 ml), and dried over sodium sulfate. After removal of solvent, the title compound was obtained which was used directly for the next step without purification. MS: Calcd.: 404. Found: [M+H]$^+$ 405.

Method 58

(S)-3-Chloro-N$^6$-(1-(4-fluorophenyl)ethyl)-N$^2$-(5-isopropoxy-1H-pyrazol-3-yl)-5-nitropyridine-2,6-diamine A mixture of 3,6-dichloro-N-(5-isopropoxy-1H-pyrazol-3-yl)-5-nitropyridin-2-amine (Method 59, 0.25 g, 0.75 mmol), (S)-1-(4-fluoro-phenyl)-ethylamine (0.13 g, 0.90 mmol) and DIEA (0.16 ml, 0.94 mmol) in n-BuOH (3 ml) was heated in a sealed tube at 145° C. for 2 hours. The solvent was removed under reduced pressure and the residue was purified by column chromatography (hexane-EtOAc=1:1) to give the title compound as a yellow solid (0.32 g, 98%). $^1$H NMR (400 MHz) δ 12.22 & 11.40 (s, 1H), 9.74 & 9.37 (s, 1H), 8.93 (d, J=7.6 Hz, 1H), 8.33 & 8.27 (s, 1H), 7.34 & 7.27 (m, 2H), 7.12 & 7.05 (m, 2H), 5.75 & 5.62 (s, 1H), 5.35 & 5.25 (m, 1H), 4.66 & 4.03 (m, 1H), 1.55 (d, J=6.4 Hz, 3H), 1.29 (d, J=6.0 Hz, 6H). MS: Calcd.: 434. Found: [M+H]$^+$ 435.

Method 59

3,6-Dichloro-N-(5-isopropoxy-1H-pyrazol-3-yl)-5-nitropyridin-2-amine

To a mixture of 2,3,6-trichloro-5-nitropyridine (2.61 g, 11.4 mmol) and DIEA (1.90 ml, 11.4 mmol) in THF (50 ml) was added 5-isopropoxy-1H-pyrazol-3-amine (1.20 g, 8.50 mmol) at 0° C. After addition, the reaction mixture was stirred at 25° C. for 5 days. The solvent was removed under reduced pressure and the resulted residue was purified by column chromatography (hexane-EtOAc=1:1) to give the title compound as a yellow solid (0.51 g, 18%). $^1$H NMR (400 MHz) δ 12.22 & 11.35 (s, 1H), 10.12 & 9.80 (s, 1H), 8.64 & 8.54 (s, 1H), 5.95 & 5.84 (s, 1H), 4.70 & 4.46 (m, 1H), 1.27-1.32 (m, 6H). MS: Calcd.: 331. Found: [M+H]$^+$ 332.

Method 60

(S)—N$^2$-(1-(4-Fluorophenyl)ethyl)pyridine-N$^6$-(5-isopropoxy-1H-pyrazol-3-yl)-2,3,6-triamine A solution of saturated ammonium chloride (3 ml) was added slowly to a suspension of (S)—N$^2$-(1-(4-fluorophenyl)ethyl)-N$^6$-(5-isopropoxy-1H-pyrazol-3-yl)-3-nitropyridine-2,6-diamine (Method 61, 0.28 g, 0.70 mmol) and zinc dust (0.23 g, 3.5 mmol) in the mixture of MeOH-THF (1:1, 20 ml). The mixture was stirred at 25° C. for 1 hour. Saturated ammonium acetate solution (5 ml) was added and the mixture was stirred for another 30 minutes. Zn dust was removed by filtration and the cake was washed with EtOAc (20 ml). The organic layer was separated, washed with brine (10 ml), and dried over sodium sulfate. After removal of solvent, the title compound was obtained which was used directly for the next step without purification. MS: Calcd.: 370. Found: [M+H]$^+$ 371.

Method 61

(S)—N$^2$-(1-(4-Fluorophenyl)ethyl)-N$^6$-(5-isopropoxy-1H-pyrazol-3-yl)-3-nitropyridine-2,6-diamine A mixture of (S)-6-chloro-N-(1-(4-fluorophenyl)ethyl)-3-nitropyridin-2-amine (Method 19, 1.08 g, 3.7 mmol), 5-isopropoxy-1H-pyrazol-3-amine (0.57 g, 4.0 mmol), and DIEA (0.80 ml, 4.6 mmol) in n-BuOH (10 ml) was heated in a sealed tube at 115° C. for 72 hours. The solvent was removed under reduced pressure and the residue was purified by chromatography (hexane-EtOAc=3:1) to give the title compound as a yellow solid (0.32 g, 22%). MS: Calcd.: 400. Found: [M+H]$^+$ 401.

Method 62

(R)-2-(3-Amino-6-(5-methyl-1H-pyrazol-3-ylamino)pyridin-2-ylamino)-2-(4-fluorophenyl)ethanol A solution of saturated ammonium chloride (3 ml) was added slowly to a suspension of (R)-2-(4-fluorophenyl)-2-(6-(5-methyl-1H-pyrazol-3-ylamino)-3-nitropyridin-2-ylamino)ethanol (Method 63, 0.29 g, 0.78 mmol) and zinc dust (0.25 g, 3.9 mmol) in a mixture of MeOH-THF (1:1, 20 ml). The mixture was stirred at 25° C. for 1 hour. Saturated ammonium acetate solution (5 ml) was added and the mixture was stirred for another 30 minutes. The Zn dust was removed by filtration and the cake was washed with EtOAc (20 ml). The organic layer was separated, washed with brine (10 ml) and dried over sodium sulfate. After removal of solvent, the title compound was obtained which was used directly for the next step without purification. MS: Calcd.: 342. Found: [M+H]$^+$ 343.

Method 63

(R)-2-(4-Fluorophenyl)-2-(6-(5-methyl-1H-pyrazol-3-ylamino)-3-nitropyridin-2-ylamino)ethanol A mixture of (2R)-2-(6-chloro-3-nitropyridin-2-ylamino)-2-(4-fluorophenyl)ethanol (Method 21, 0.36 g, 1.2 mmol), 5-methyl-1H-pyrazol-3-amine (0.14 g, 1.4 mmol), and DIEA (0.25 ml, 1.4 mmol) in n-BuOH (5 ml) was heated in a sealed tube at 90° C. for 6 days. The solvent was removed under reduced pressure and the residue was purified by column chromatography (EtOAc) to give the title compound as a yellow solid (0.31 g, 73%). $^1$H NMR (400 MHz) δ 12.06 (s, 1H), 10.40 (br s, 1H), 9.58 (br s, 1H), 8.11 (d, J=9.2 Hz, 1H), 7.40 (m, 2H), 7.16 (m, 2H), 6.20 (br s, 1H), 6.02 (s, 1H), 5.29 (br, 1H), 5.24 (t, J=4.4 Hz, 1H), 3.85 (m, 1H), 3.74 (m, 1H), 2.20 (s, 3H). MS: Calcd.: 372. Found: [M+H]$^+$ 373.

Utility

The compounds of the present invention have utility for the treatment of cancer by inhibiting the tyrosine kinases, particularly the Trks and more particularly Trk A and B. Methods of treatment target tyrosine kinase activity, particularly the Trk activity and more particularly Trk A and B activity, which is involved in a variety of cancer related processes. Thus, inhibitors of tyrosine kinase, particularly the Trks and more particularly Trk A and B, are expected to be active against neoplastic disease such as carcinoma of the breast, ovary, lung, colon, prostate or other tissues, as well as leukemias and lymphomas, tumours of the central and peripheral nervous system, and other tumour types such as melanoma, fibrosarcoma and osteosarcoma. Tyrosine kinase inhibitors, particularly the Trk inhibitors and more particularly Trk A and B inhibitors are also expected to be useful for the treatment other proliferative diseases including but not limited to autoimmune, inflammatory, neurological, and cardiovascular diseases.

In addition, the compounds of the invention are expected to be of value in the treatment or prophylaxis of cancers selected with up regulated of constitutively activated Trk kinases, including but not limited to, oncogenic rearrangements leading to ETV6-TrkC fusions, TRP-TrkA fusions proteins, AML-ETO (t8;21), autocrine or paracrine signalling leading to elevated serum levels of NGF, BDNF, neurotropins or tumours with constitutively active Trk associated with disease aggressiveness, tumour growth and proliferation or survival signalling.

Compounds of the present invention have been shown to inhibit tyrosine kinases, particularly the Trks and more particularly Trk A and B, as determined by the Trk A Assay described herein.

Compounds provided by this invention should also be useful as standards and reagents in determining the ability of a potential pharmaceutical to inhibit tyrosine kinases, particularly the Trks and more particularly Trk A and B. These would be provided in commercial kits comprising a compound of this invention Trk A Assay Format Trk A kinase activity was measured for its ability to phosphorylate synthetic tyrosine residues within a generic polypeptide substrate using an Amplified Luminescent Proximity Assay (Alphascreen) technology (PerkinElmer, 549 Albany Street, Boston, Mass.).

To measure Trk A kinase activity, the intracellular domain of a HIS-tagged human Trk A kinase (amino acids 442-796 of Trk A, Swiss-Prot Primary Accession Number P04629) was expressed in SF9 cells and purified using standard nickel column chromatography. After incubation of the kinase with a biotinylated substrate and adenosine triphosphate (ATP) for 20 minutes at room temperature, the kinase reaction was stopped by the addition of 30 mM ethylenediaminetetraacetic acid (EDTA). The reaction was performed in 384 well microtitre plates and the reaction products were detected with the addition of strepavidin coated Donor Beads and phospho-tyrosine-specific antibodies coated Acceptor Beads using the EnVision Multilabel Plate Reader after an overnight incubation at room temperature.

| Peptide substrate | PolyEY-biotin (PGT-bio.) |
| --- | --- |
| ATP Km | 70 μM |
| Assay conditions | 0.838 ng/ml Trk A, 9 mM HEPES, 45 μg/ml BSA, 10 mM MnCl$_2$, 5 nM PGT-bio, 0.01% Triton ® X-100, 70 μM ATP |
| Incubation | 20 minutes, room temperature |
| Termination/Detection conditions | 6.3 mM HEPES, 30 mM EDTA, 525 μg/mL BSA, 40 mM NaCl, 0.007% Triton ® X-100, 12 ng/ml of Donor Beads, 12 ng/ml of Acceptor Beads |
| Detection incubation | overnight, room temperature |
| Fluometers settings | Excitation = 680 nM Emission = 570 nM Excitation Time = 180 ms Total Measurement Time = 550 ms |

Although the pharmacological properties of the compounds of the formula (I) vary with structural change, in general activity possessed by compounds of the formula (I) may be demonstrated at IC$_{50}$ concentrations (concentrations to achieve 50% inhibition) or doses in the range of (0.01 μM to 10 μM).

When tested in the above in-vitro assay the Trk inhibitory activity of the following examples was measured at the following IC$_{50}$s.

| Ex | IC$_{50}$ (μM) |
| --- | --- |
| 5 | 0.063 |
| 6 | 0.049 |
| 18 | 0.011 |

The invention claimed is:

1. A compound of formula (I):

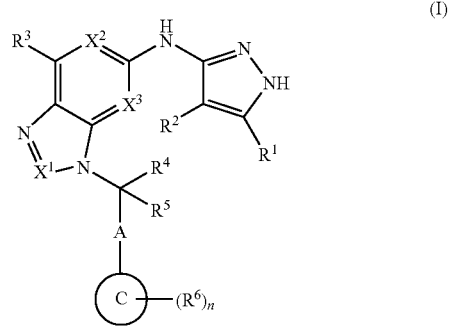

wherein:
R$^1$ and R$^2$ are independently selected from hydrogen, halo, nitro, cyano, hydroxy, trifluoromethoxy, amino, carboxy, carbamoyl, mercapto, sulphamoyl, C$_{1-6}$alkyl, C$_{2-6}$alkenyl, C$_{2-6}$alkynyl, C$_{1-6}$alkoxy, C$_{1-6}$alkanoyl, C$_{1-6}$alkanoyloxy, N—(C$_{1-6}$alkyl)amino, N,N—(C$_{1-6}$alkyl)$_2$amino, C$_{1-6}$alkanoylamino, N—(C$_{1-6}$alkyl)carbamoyl, N,N—(C$_{1-6}$alkyl)$_2$carbamoyl, C$_{1-6}$alkylS(O)$_a$ wherein a is 0 to 2, C$_{1-6}$alkoxycarbonyl, N—(C$_{1-6}$alkyl)sulphamoyl, N,N—(C$_{1-6}$alkyl)$_2$sulphamoyl, C$_{1-6}$alkylsulphonylamino, carbocyclyl or heterocyclyl; wherein R$^1$ and R$^2$ independently of each other may be optionally substituted on carbon by one or more R$^7$; and wherein if said heterocyclyl contains an —NH— moiety that nitrogen may be optionally substituted by a group selected from $R^8$;

$X^1$, $X^2$ and $X^3$ are independently =N— or =CR$^9$—;

$R^3$ and $R^9$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl-$R^{10}$— or heterocyclyl-$R^{11}$—; wherein $R^3$ and $R_9$ independently of each other may be optionally substituted on carbon by one or more $R^{12}$; and wherein if said heterocyclyl contains an —NH— moiety that nitrogen may be optionally substituted by a group selected from $R^{13}$;

$R^4$ and $R^5$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^4$ and $R^5$ independently of each other may be optionally substituted on carbon by one or more $R^{14}$; and wherein if said heterocyclyl contains an —NH— moiety that nitrogen may be optionally substituted by a group selected from $R^{15}$;

A is a direct bond or $C_{1-2}$alkylene; wherein said $C_{1-2}$alkylene may be optionally substituted by one or more Ring C is carbocyclyl or heterocyclyl; wherein if said heterocyclyl contains an —NH— moiety that nitrogen may be optionally substituted by a group selected from $R^{17}$;

$R^6$ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^6$ may be optionally substituted on carbon by one or more $R^{18}$; and wherein if said heterocyclyl contains an —NH— moiety that nitrogen may be optionally substituted by a group selected from $R^{19}$;

n is 0, 1, 2 or 3; wherein the values of $R^6$ may be the same or different;

$R^7$, $R^{12}$, $R^{14}$, $R^{16}$ and $R^{18}$ and are independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl-$R^{20}$— or heterocyclyl-$R^{21}$—; wherein $R^7$, $R^{12}$, $R^{14}$, $R^{16}$ and $R^{18}$ independently of each other may be optionally substituted on carbon by one or more $R^{22}$; and wherein if said heterocyclyl contains an —NH— moiety that nitrogen may be optionally substituted by a group selected from $R^{23}$;

$R^8$, $R^{13}$, $R^{15}$, $R^{17}$, $R^{19}$ and $R^{23}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulphonyl; wherein $R^8$, $R^{13}$, $R^{15}$, $R^{17}$, $R^{19}$ and $R^{23}$ independently of each other may be optionally substituted on carbon by on or more $R^{22}$ and $R^{24}$ are independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^{22}$ and $R^{24}$ independently of each other may be optionally substituted on carbon by one or more $R^{25}$; and wherein if said heterocyclyl contains an —NH— moiety that nitrogen may be optionally substituted by a group selected from $R^{26}$;

$R^{10}$, $R^{11}$, $R^{20}$ and $R^{21}$ are independently selected from a direct bond, —O—, —N($R^{27}$)—, —C(O)—, —N($R^{28}$)C(O)—, —C(O)N($R^{29}$)—, —S(O)$_s$—, —SO$_2$N($R^{30}$)— or —N($R^{31}$)SO$_2$—; wherein $R^{27}$, $R^{28}$ $R^{29}$, $R^{30}$ and $R^{31}$ are independently selected from hydrogen or $C_{1-6}$alkyl and s is 0-2;

$R^{25}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{26}$ is selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulphonyl;

or a pharmaceutically acceptable salt thereof.

2. A compound of formula (I), or a pharmaceutically acceptable salt thereof, as claimed in claim 1 wherein $R^1$ is selected from $C_{1-6}$alkyl, $C_{1-6}$alkoxy or carbocyclyl.

3. A compound of formula (I), or a pharmaceutically acceptable salt thereof, as claimed in claim 1 wherein $R^2$ is hydrogen.

4. A compound of formula (I), or a pharmaceutically acceptable salt thereof, as claimed claim 1 wherein $R^3$ and $R^9$ are independently selected from hydrogen, halo, hydroxy and $C_{1-6}$alkyl.

5. A compound of formula (I), or a pharmaceutically acceptable salt thereof, as claimed in claim 1 wherein $R^4$ and $R^5$ are independently selected from hydrogen or $C_{1-6}$alkyl; and wherein $R^4$ and $R^5$ independently of each other may be optionally substituted on carbon by one or more $R^{14}$; wherein $R^{14}$ is hydroxy.

6. A compound of formula (I), or a pharmaceutically acceptable salt thereof, as claimed in claim 1 wherein A is a direct bond.

7. A compound of formula (I), or a pharmaceutically acceptable salt thereof, as claimed in claim 1 wherein Ring C is phenyl.

8. A compound of formula (I), or a pharmaceutically acceptable salt thereof, as claimed in claim 1 wherein $R^6$ is halo.

9. A compound of formula (I), or a pharmaceutically acceptable salt thereof, as claimed in claim 1 wherein n is 0 or 1.

10. A compound of formula (I):

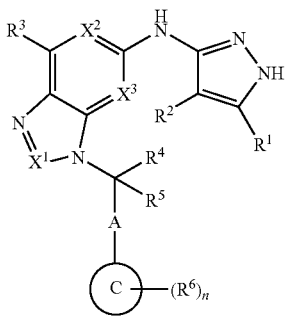

(I)

wherein:
R$^1$ is selected from methyl, t-butyl, isopropoxy or cyclopropyl;
R$^2$ is hydrogen;
X$^1$, X$^2$ and X$^3$ are independently =N— or =CR$^9$—;
R$^3$ and R$^2$ are independently selected from hydrogen, fluoro, chloro, hydroxy and methyl;
R$^4$ and R$^5$ are independently selected from hydrogen, methyl or hydroxymethyl;
A is a direct bond;
Ring C is phenyl;
R$^6$ is fluoro; and
n is 1;
or a pharmaceutically acceptable salt thereof.

11. A compound of formula (I):

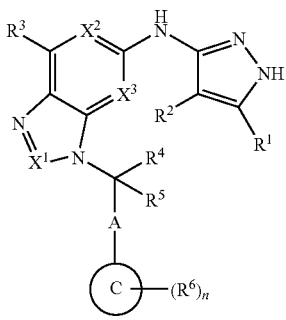

(I)

selected from:
(S)—N-(5-cyclopropyl-1H-pyrazol-3-yl)-3-(1-(4-fluorophenyl)ethyl)-3H-imidazo[4,5-b]pyridin-5-amine;
(R)-2-(5-(5-cyclopropyl-1H-pyrazol-3-ylamino)-3H-imidazo[4,5-b]pyridin-3-yl)-2-(4-fluorophenyl)ethanol;
(S)-6-chloro-N-(5-cyclopropyl-1H-pyrazol-3-yl)-3-(1-(4-fluorophenyl)ethyl)-3H-imidazo[4,5-b]pyridin-5-amine;

(R)-2-(6-chloro-5-(5-cyclopropyl-1H-pyrazol-3-ylamino)-3H-imidazo[4,5-b]pyridin-3-yl)-2-(4-fluorophenyl)ethanol;
(R)-2-(6-chloro-5-(5-methyl-1H-pyrazol-3-ylamino)-3H-imidazo[4,5-b]pyridin-3-yl)-2-(4-fluorophenyl)ethanol;
(S)-6-fluoro-3-(1-(4-fluorophenyl)ethyl)-N-(5-methyl-1H-pyrazol-3-yl)-3H-imidazo[4,5-b]pyridin-5-amine;
(R)-2-(5-(5-cyclopropyl-1H-pyrazol-3-ylamino)-6-fluoro-3H-imidazo[4,5-b]pyridin-3-yl)-2-(4-fluorophenyl)ethanol;
(S)—N-(5-cyclopropyl-1H-pyrazol-3-yl)-6-fluoro-3-(1-(4-fluorophenyl)ethyl)-3H-imidazo[4,5-b]pyridin-5-amine;
(S)-6-fluoro-3-(1-(4-fluorophenyl)ethyl)-N-(5-isopropoxy-1H-pyrazol-3-yl)-3H-imidazo[4,5-b]pyridin-5-amine; and
(S)-6-chloro-3-(1-(4-fluorophenyl)ethyl)-N-(5-isopropoxy-1H-pyrazol-3-yl)-3H-imidazo[4,5-b]pyridin-5-amine;
or a pharmaceutically acceptable salt thereof.

12. A process for preparing a compound of formula (I) or a pharmaceutically acceptable salt thereof which process, wherein variable groups are, unless otherwise specified, as defined in claim 1, wherein said process is selected from:

Process a) reaction of a compound of formula (II):

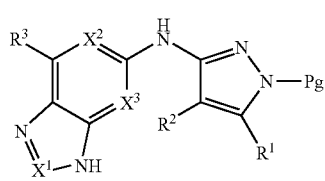

(II)

wherein Pg is a nitrogen protecting group; with a compound of formula (III):

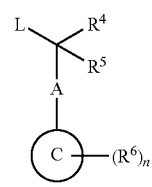

(III)

wherein L is a displaceable group to produce a compound of formula (I);

Process b) reaction of a compound of formula (II) with an epoxide of formula (IV) to produce a compound of formula (I) wherein $R^4$ is hydroxymethyl and $R^5$ is hydrogen:

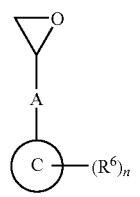

(IV)

Process c) reacting a compound of formula (V):

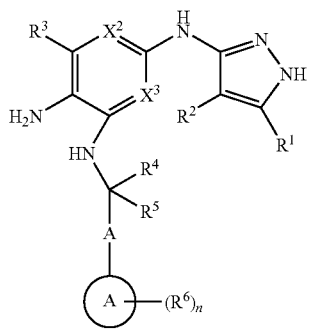
(V)

with a compound of formula (VI) to produce a compound of formula (I) wherein $X^1$ is $=CR^9-$:

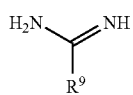
(VI)

Process d) reacting a compound of formula (V) with aqueous $NaNO_2$ solution to produce a compound of formula (I) wherein $X^1$ is $=N-$;

Process e) reacting a compound of formula (VII):

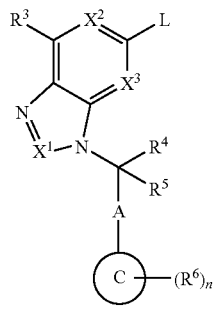
(VII)

wherein L is a displaceable group; with an amine of formula (VIII):

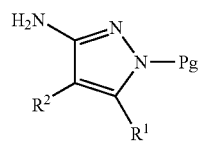
(VIII)

wherein Pg is a nitrogen protecting group to produce a compound of formula (I);

Process f) reacting a compound of formula (IX):

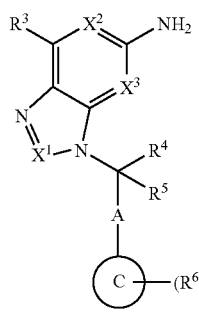
(IX)

with a compound of formula (X):

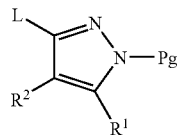
(X)

wherein L is a displaceable group to produce a compound of formula (I);

and thereafter if necessary:
i) converting a compound of the formula (I) into another compound of the formula (I);
ii) removing any protecting groups;
iii) forming a pharmaceutically acceptable salt.

13. A pharmaceutical composition comprising a compound of formula (I), or a pharmaceutically acceptable salt thereof, as claimed in claim 1, together with at least one pharmaceutically acceptable carrier, diluent or excipient.

* * * * *